US012636246B2

(12) United States Patent
Menzer et al.

(10) Patent No.: US 12,636,246 B2
(45) **Date of Patent: *May 26, 2026**

(54) PROCESS FOR COLOURING HAIR KERATIN FIBERS, COMPRISING THE APPLICATION OF A COMPOSITION COMPRISING AT LEAST ONE (POLY)CARBODIIMIDE COMPOUND AND A COMPOSITION COMPRISING AT LEAST ONE ASSOCIATIVE POLYMER AND A PARTICULAR COMPOUND

(71) Applicant: L'Oreal, Paris (FR)

(72) Inventors: Lindsay Menzer, St. Ouen (FR); Chrystel Pourille, St. Ouen (FR); Thin Hinane Hammiche, St. Ouen (FR)

(73) Assignee: L'Oreal, Paris (FR)

( * ) Notice: Subject to any disclaimer, the term of this patent is extended or adjusted under 35 U.S.C. 154(b) by 335 days.

This patent is subject to a terminal disclaimer.

(21) Appl. No.: 18/549,555

(22) PCT Filed: Mar. 10, 2022

(86) PCT No.: PCT/EP2022/056195

§ 371 (c)(1),
(2) Date: Sep. 7, 2023

(87) PCT Pub. No.: WO2022/189570

PCT Pub. Date: Sep. 15, 2022

(65) Prior Publication Data

US 2024/0197614 A1 Jun. 20, 2024

(30) Foreign Application Priority Data

Mar. 10, 2021 (FR) ...................................... 2102356

(51) Int. Cl.

| | |
|---|---|
| ***A61Q 5/06*** | (2006.01) |
| ***A61K 8/19*** | (2006.01) |
| ***A61K 8/31*** | (2006.01) |
| ***A61K 8/34*** | (2006.01) |
| ***A61K 8/81*** | (2006.01) |
| ***A61K 8/88*** | (2006.01) |
| ***A61K 8/891*** | (2006.01) |
| ***A61K 8/898*** | (2006.01) |
| ***A61Q 5/00*** | (2006.01) |
| ***A61Q 5/10*** | (2006.01) |

(52) U.S. Cl.

CPC .................. *A61K 8/88* (2013.01); *A61K 8/19* (2013.01); *A61K 8/31* (2013.01); *A61K 8/345* (2013.01); *A61K 8/8147* (2013.01); *A61K 8/8152* (2013.01); *A61K 8/891* (2013.01); *A61K 8/898* (2013.01); *A61Q 5/065* (2013.01); *A61K 2800/43* (2013.01); *A61K 2800/87* (2013.01); *A61K 2800/882* (2013.01); *A61K 2800/884* (2013.01)

(58) Field of Classification Search

CPC . A61Q 5/065; A61Q 5/10; A61Q 5/06; A61Q 5/00; A61Q 5/08; A61K 8/8152; A61K 8/87; A61K 8/345; A61K 2800/43; A61K 2800/4324; A61K 2800/884; A61K 2800/882; A61K 8/88; A61K 2800/594; A61K 2800/88

See application file for complete search history.

(56) References Cited

U.S. PATENT DOCUMENTS

| | | | |
|---|---|---|---|
| 2017/0189314 | A1 | 7/2017 | Elsen-Wahrer et al. |
| 2018/0371237 | A1 | 12/2018 | Tsukamoto et al. |

FOREIGN PATENT DOCUMENTS

| | | |
|---|---|---|
| CN | 108883313 | 11/2018 |
| FR | 1 567 219 | 5/1969 |
| WO | WO2015/088126 | 6/2015 |
| WO | WO2019/006331 | 1/2019 |
| WO | WO2019/211050 | 11/2019 |

OTHER PUBLICATIONS

International Search Report and Written Opinion for International Application No. PCT/EP2022/0562195 (filed Mar. 10, 2022), mailed Jun. 23, 2022, 12 pages).

A. J. Derksen: "Polycarbodiimides as classification-free and easy to use crosslinkers for water-based coatings", Jul. 8, 2017 (Jul. 8, 2017), XP055719203, Retrieved from the Internet: URL:https://web.archive.org/web/20170708064027/https://www.pcimag.com/ext/resources/ WhitePapers/2017/Stahl-Polymers-White-paper-PolyCarbodiimide-Crosslinkers.pdf [retrieved on Jul. 30, 2020].

*Primary Examiner* — Tracy Liu
(74) *Attorney, Agent, or Firm* — CHRISTENSEN O'CONNOR JOHNSON KINDNESS PLLC

(57) ABSTRACT

The present invention relates to a process for colouring hair keratin fibers, in particular the hair, comprising the application of a composition A and a composition B to said hair keratin fibers, in which: composition A comprises at least one (poly)carbodiimide compound, and composition B comprises: at least one associative polymer; and at least one compound, different from the associative polymers, containing at least one carboxylic acid group; at least one compound, preferably at least two compounds, containing at least one hydroxyl function; composition A and/or composition B comprising at least one colouring agent chosen from pigments, direct dyes and mixtures thereof; and in which composition A and composition B are applied simultaneously or sequentially to the hair keratin fibers. The present invention also relates to a device for colouring hair keratin fibers.

22 Claims, No Drawings

PROCESS FOR COLOURING HAIR KERATIN FIBERS, COMPRISING THE APPLICATION OF A COMPOSITION COMPRISING AT LEAST ONE (POLY)CARBODIIMIDE COMPOUND AND A COMPOSITION COMPRISING AT LEAST ONE ASSOCIATIVE POLYMER AND A PARTICULAR COMPOUND

The present application is a National Stage Application of PCT/EP2022/056195, filed Mar. 10, 2022, which claims the benefit of FR2102356, filed Mar. 10, 2021, the disclosures of which are incorporated herein in their entirety.

The present invention relates to a process for colouring hair keratin fibers comprising the application of a composition A and a composition B to the hair keratin fibers, in which composition A comprises at least one (poly)carbodiimide compound and composition B comprises at least one associative polymer, at least one compound, different from the associative polymers, containing at least one carboxylic acid group, and at least one compound containing at least one hydroxyl function, composition A and/or composition B comprising at least one colouring agent chosen from pigments, direct dyes, and mixtures thereof, and in which composition A and composition B are applied simultaneously or sequentially to the hair keratin fibers.

The present invention also relates to a device for colouring hair keratin fibers.

TECHNICAL FIELD

In the field of colouring hair keratin fibers, in particular human hair keratin fibers, it is already known practice to colour hair keratin fibers via various techniques using direct dyes or pigments for non-permanent colouring, or dye precursors for permanent colouring.

There are essentially three types of process for colouring the hair:

a) "permanent" colouring, the function of which is to afford a substantial modification to the natural colour and which uses oxidation dyes which penetrate into the hair fibre and forms the dye via an oxidative condensation process;

b) non-permanent, semi-permanent or direct colouring, which does not use the oxidative condensation process and withstands four or five shampoo washes; it consists in colouring hair keratin fibers with colour compositions containing direct dyes;

c) temporary colouring, which gives rise to a modification of the natural colour of the hair that remains from one shampoo wash to the next, and which serves to enhance or correct a shade that has already been obtained. It may also be likened to a "makeup" process.

For this last type of colouring, it is known practice to use coloured polymers formed by grafting one or more dyes of azo, triphenylmethane, azine, indoamine or anthraquinone nature onto a polymer chain. These coloured polymers are not entirely satisfactory, notably as regards the uniformity of the colouring obtained and its resistance, not to mention the problems associated with their manufacture and notably with their reproducibility.

Another colouring method consists in using pigments. Specifically, the use of pigment on the surface of hair keratin fibers generally makes it possible to obtain visible colourings on dark hair, since the surface pigment masks the natural colour of the fibre. However, the colourings obtained via this colouring method have the drawback of having poor resistance to shampoo washing and also to external agents such as sebum, perspiration, brushing and/or rubbing.

Furthermore, temporary hair colour compositions may moreover have working qualities that are not entirely satisfactory, notably in terms of texture, and ease and/or uniformity of spreading on the head of hair.

There is thus still a need for a process for colouring hair keratin fibers which has the advantage of obtaining a smooth and uniform coloured coating on the hair, while at the same time forming a coating that is persistent with respect to shampoo washing and to the various attacking factors to which the hair may be subjected such as brushing and/or friction without degradation of the hair, and in which the compositions used in the context of said process have good stability over time and good storage over time, i.e. good protection against microorganisms, and also good working qualities.

Thus, the aim of the present invention is to develop a process for colouring hair keratin fibers which has the advantage of obtaining a smooth and uniform coloured coating on the hair, while at the same time forming a coating that is persistent with respect to shampoo washing and to the various attacking factors to which the hair may be subjected such as brushing and/or friction without degradation of the hair, and in which the compositions used in the context of said process have good stability over time and good storage over time, i.e. good protection against microorganisms, and also good working qualities.

DISCLOSURE OF THE INVENTION

One subject of the present invention is thus a process for colouring hair keratin fibers comprising the application of a composition A and a composition B to the hair keratin fibers, in which:

composition A comprises at least one (poly)carbodiimide compound, and composition B comprises:

at least one associative polymer;

at least one compound, different from the associative polymers, containing at least one carboxylic acid group and at least one compound, preferably at least two compounds, containing at least one hydroxyl function;

composition A and/or composition B comprising at least one colouring agent chosen from pigments, direct dyes and mixtures thereof; and in which composition A and composition B are applied simultaneously or sequentially to the hair keratin fibers.

In one variant of the invention, a composition C is obtained by extemporaneous mixing at the time of use of at least one composition A as defined previously and of at least one composition B as defined previously. In this variant, composition C, obtained by mixing composition A and composition B, is applied to the hair keratin fibers.

In another variant, composition A as defined previously and composition B as defined previously are applied simultaneously to the hair keratin fibers.

In another variant, composition A and composition B are applied sequentially to the hair keratin fibers, composition A possibly being applied to the hair keratin fibers before composition B, or vice versa.

The present invention also relates to a device for colouring hair keratin fibers, comprising at least two compartments containing:

in a first compartment (E1), a composition A as defined previously; and in a second compartment (E2), a composition B as defined previously;

optionally, in a third compartment (E3), a composition D as defined below.

Via the use of this colouring process on hair keratin fibers, coloured coatings are obtained on the hair that make it possible to obtain a colouring that is visible on all types of hair in a manner that is persistent with respect to shampoo washing, while at the same time preserving the physical qualities of the hair keratin fibers. Such a coating may be resistant to the external attacking factors to which the hair may be subjected, such as blow-drying and perspiration. It makes it possible in particular to obtain a smooth and uniform deposit.

Moreover, the compositions used in the context of the colouring process according to the invention have good stability over time, in particular after periods of storage at room temperature or at temperatures ranging up to 45° C. The compositions used in the context of the colouring process according to the invention also have good storage over time, i.e. good protection against microorganisms, in particular after periods of storage of up to 2 months at room temperature or at temperatures ranging up to 55° C.

Furthermore, the compositions used in the context of the process according to the invention have good working qualities, in particular in terms of texture, and ease and uniformity of spreading on the hair, while at the same time minimizing any problems of running.

For the purposes of the present invention, the term "colouring that is persistent with respect to shampoo washing" means that the colouring obtained persists after one shampoo wash, preferably after three shampoo washes, more preferentially after five shampoo washes.

Other subjects, characteristics, aspects and advantages of the invention will emerge even more clearly on reading the description and the examples that follow.

In the text hereinbelow, unless otherwise indicated, the limits of a range of values are included in that range, notably in the expressions "between" and "ranging from . . . to . . . ".

The term "at least one" means one or more.

The invention is not limited to the illustrated examples. The characteristics of the various examples may notably be combined within variants which are not illustrated.

For the purposes of the present invention and unless otherwise indicated:

an "alkyl" radical denotes a linear or branched saturated radical containing, for example, from 1 to 20 carbon atoms;

an "aminoalkyl" radical denotes an alkyl radical as defined previously, said alkyl radical comprising an $NH_2$ group;

a "hydroxyalkyl" radical denotes an alkyl radical as defined previously, said alkyl radical comprising an OH group;

an "alkylene" radical denotes a linear or branched divalent saturated $C_2$-$C_4$ hydrocarbon-based group such as methylene, ethylene or propylene;

a "cycloalkyl" or "alicycloalkyl" radical denotes a cyclic saturated monocyclic or bicyclic, preferably monocyclic, hydrocarbon-based group comprising from 1 to 3 rings, preferably 2 rings, and comprising from 3 to 24 carbon atoms, in particular comprising from 3 to 20 carbon atoms, more particularly from 3 to 13 carbon atoms, even more particularly from 3 to 12 carbon atoms, preferably between 5 and 10 carbon atoms, such as cyclopropyl, cyclopentyl, cyclohexyl, cycloheptyl or norbornyl, in particular cyclopropyl, cyclopentyl or cyclohexyl, it being understood that the cycloalkyl radical may be substituted with one or more ($C_1$-$C_4$) alkyl groups such as methyl; preferably, the cycloalkyl radical is then an isobornyl group;

a "cycloalkylene" radical denotes a divalent cycloalkyl group with "cycloalkyl" as defined previously, preferably of $C_3$-$C_{12}$;

an "aryl" radical is a monocyclic, bicyclic or tricyclic, fused or non-fused, unsaturated and aromatic hydrocarbon-based cyclic radical, comprising from 6 to 14 carbon atoms, preferably between 6 and 12 carbon atoms; preferably, the aryl group comprises 1 ring of 6 carbon atoms such as phenyl, naphthyl, anthryl, phenanthryl and biphenyl, it being understood that the aryl radical may be substituted with one or more ($C_1$-$C_4$)alkyl groups such as methyl, preferably tolyl, xylyl, or methylnaphthyl; preferably, the aryl group represents phenyl;

an "arylene" radical is a divalent aryl radical with "aryl" as defined previously; preferably, arylene represents phenylene;

a "heterocyclic" radical denotes a saturated or unsaturated, non-aromatic or aromatic, monocyclic or polycyclic hydrocarbon-based radical, comprising one or more heteroatoms, preferably from 1 to 5 atoms chosen from O, S or N, including from 3 to 20 ring members, preferably between 5 and 10 ring members, such as imidazolyl, pyrrolyl and furanyl;

a "heterocycloalkylene" radical is a divalent heterocyclic group with "heterocyclic" as defined previously;

an "aryloxy" radical denotes an aryl-oxy with "aryl" as defined previously;

an "alkoxy" radical denotes an alkyl-oxy radical with "alkyl" as defined previously;

an "acyloxy" radical denotes an ester radical R—C(O)—O— with R being an alkyl group as defined previously;

a "reactive" group is a group that is capable of forming a covalent bond with another identical or different group, by chemical reaction.

The term "hair keratin fibers" means the hair.

For the purposes of the present invention, the expression "hair" means the hair of the head. It does not refer to eyelashes, eyebrows and body hair.

Polycarbodiimide Compound

Composition A according to the invention used in the context of the colouring process according to the invention comprises at least one (poly)carbodiimide compound.

The composition may comprise at least two different (poly)carbodiimide compounds, present as a mixture in the composition.

The term "(poly)carbodiimide compound" means a compound comprising one or more carbodiimide groups, preferably at least two carbodiimide groups, more preferentially at least three carbodiimide groups; in particular, the number of carbodiimide groups does not exceed 200, preferably 150, more preferentially 100.

The term "carbodiimide group" means a divalent linear triatomic fraction of general formula —(N═C═N)—.

The (poly)carbodiimide compound(s) according to the invention may optionally comprise in their structure one or more reactive groups different from carbodiimide groups, chosen from alkoxysilyl, hydroxysilyl, acetoxysilyl, vinylsilyl, acrylalkylsilyl, methacrylalkylsilyl, crotonylalkylsilyl, carboxyanhydridoalkylsilyl, carboxyalkylsilyl, hydroxyalkylsilyl, aldehydoalkylsilyl, mercaptoalkylsilyl, norbornenylsilyl, acylpentadienylalkylsilyl, maleimidoalkylsilyl, sulfonylalkylsilyl, (meth)acrylalkyl, crotonylalkyl, alkylepoxide such as propylepoxide or butylepoxide and azacyclopropane groups.

The reactive group(s) other than the carbodiimide groups may be side or end groups. Preferably, the (poly)carbodiimide compound(s) comprise one or more end groups different from carbodiimide groups, preferably one or more end groups chosen from alkoxysilyl, hydroxysilyl, acetoxysilyl, vinylsilyl, acrylalkylsilyl, methacrylalkylsilyl, crotonylalkylsilyl, carboxyanhydridoalkylsilyl, carboxyalkylsilyl, hydroxyalkylsilyl, aldehydoalkylsilyl, mercaptoalkylsilyl, norbornenylsilyl, acylpentadienylalkylsilyl, maleimidoalkylsilyl, sulfonylalkylsilyl, (meth)acrylalkyl, crotonylalkyl, alkylepoxide such as propylepoxide or butylepoxide and azacyclopropane groups.

According to a particular embodiment, the (poly)carbodiimide compound is chosen from the compounds of formula (I) below:

(I)

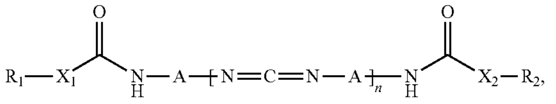

in which:

$X_1$ and $X_2$ independently represent an oxygen atom O, a sulfur atom S or an NH group;

$R_1$ and $R_2$ independently represent a group chosen from a hydrocarbon-based radical, preferably alkyl, optionally interrupted with one or more heteroatoms, a group chosen from alkoxysilyl, hydroxysilyl, acetoxysilyl, vinylsilyl, acrylalkylsilyl, methacrylalkylsilyl, crotonylalkylsilyl, carboxyanhydridoalkylsilyl, carboxyalkylsilyl, hydroxyalkylsilyl, aldehydoalkylsilyl, mercaptoalkylsilyl, norbornenylsilyl, acylpentadienylalkylsilyl, maleimidoalkylsilyl, sulfonylalkylsilyl, (meth)acrylalkyl, crotonylalkyl, alkylepoxide such as propylepoxide or butylepoxide and azacyclopropane groups, and a hydrocarbon-based radical, preferably alkyl, optionally interrupted with one or more heteroatoms and with one or more groups chosen from alkoxysilyl, hydroxysilyl, acetoxysilyl, vinylsilyl, acrylalkylsilyl, methacrylalkylsilyl, crotonylalkylsilyl, carboxyanhydridoalkylsilyl, carboxyalkylsilyl, hydroxyalkylsilyl, aldehydoalkylsilyl, mercaptoalkylsilyl, norbornenylsilyl, acylpentadienylalkylsilyl, maleimidoalkylsilyl, sulfonylalkylsilyl, (meth)acrylalkyl, crotonylalkyl, alkylepoxide such as propylepoxide or butylepoxide and azacyclopropane groups;

n denotes an integer ranging from 1 to 1000; and

A is a monomer chosen from the compounds below:

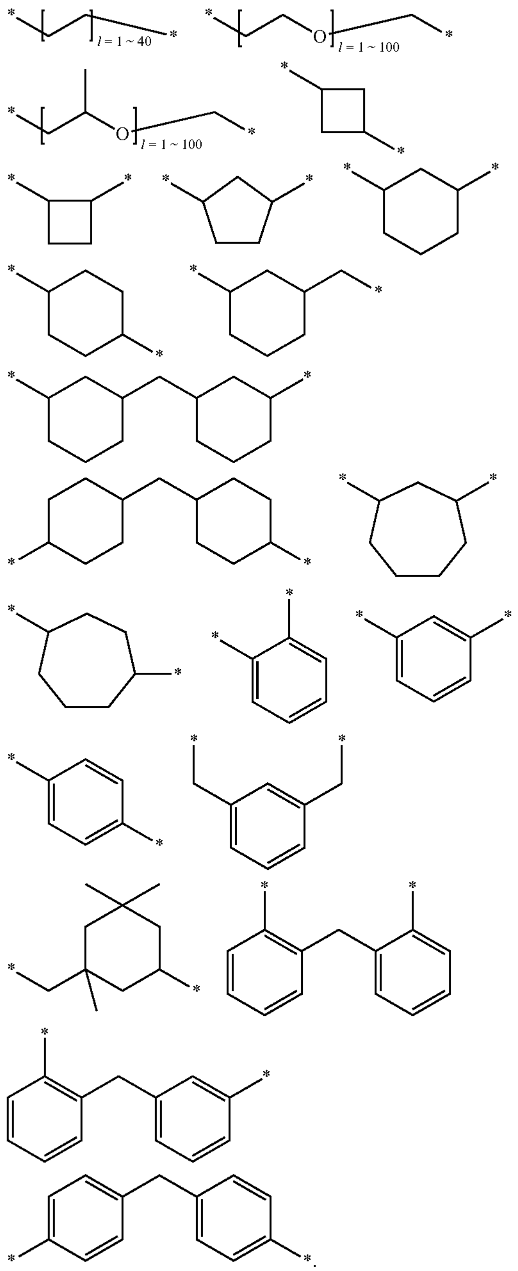

According to another embodiment, the (poly)carbodiimide compound is chosen from the compounds of formula (Ia) below:

(Ia)

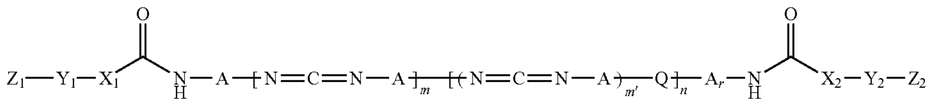

in which:

$X_1$ and $X_2$ independently represent an oxygen atom O, a sulfur atom S or an NH group;

$Y_1$ and $Y_2$ independently represent a divalent organic radical chosen from a saturated $C_1$ to $C_{36}$ aliphatic group or a $C_6$ to $C_{24}$ aromatic or alkylaromatic group, the aliphatic or aromatic group optionally comprising one or more non-pendent heteroatoms, such as a nitrogen atom, an oxygen atom, a sulfur atom, or combinations thereof;

$Z_1$ and $Z_2$ independently represent a reactive end group or an inert end group;

as inert end group, $Z_1$ and $Z_2$ may represent, independently, a saturated, linear or branched or cyclic $C_1$ to $C_{50}$ aliphatic group, or a $C_6$ to $C_{18}$ aromatic group, said aliphatic and aromatic groups optionally comprising from 1 to 10 heteroatoms chosen from nitrogen, oxygen, sulfur and combinations thereof, and the aliphatic or aromatic group may be partially or totally fluorinated; in this variant, $Z_1$ and $Z_2$ comprise a bonding group CG connecting $Z_1$ to $Y_1$ and $Z_2$ to $Y_2$, the group CG possibly being a single covalent bond, a saturated C—C bond, an unsaturated covalent C—C bond, an amide group, an ester group, a carbonate group, a thioester group, an ether group, a urethane group, a thiourethane group or a urea group;

as reactive end group, $Z_1$ and $Z_2$ may be chosen from alkoxysilyl, hydroxysilyl, acetoxysilyl, vinylsilyl, acrylalkylsilyl, methacrylalkylsilyl, crotonylalkylsilyl, carboxyanhydridoalkylsilyl, carboxyalkylsilyl, hydroxyalkylsilyl, aldehydoalkylsilyl, mercaptoalkylsilyl, norbornenylsilyl, acylpentadienylalkylsilyl, maleimidoalkylsilyl, sulfonylalkylsilyl, (meth)acrylalkyl, crotonylalkyl, alkylepoxide such as propylepoxide or butylepoxide and azacyclopropane groups;

Q represents an organopolymer or an organooligomer comprising repeating units of saturated, linear or branched or cyclic aliphatic groups, or of aromatic groups or alkylaromatic groups, coupled via carbonate, ester, ether, amide, urethane or urea repeating bonds or combinations thereof;

A represents a divalent aliphatic, aromatic, alkylaromatic or linear, saturated, branched or cyclic radical containing from 2 to 30 carbon atoms, which may optionally comprise one or more non-pendent heteroatoms such as a nitrogen atom, an oxygen atom, a sulfur atom, or combinations thereof, in the aliphatic chain or the aromatic chain;

r denotes an integer equal to 0 or 1;

m denotes an integer ranging from 0 to 1000, preferably equal to 0 or 1;

m' denotes an integer ranging from 0 to 1000, preferably equal to 0 or 1;

n denotes an integer ranging from 0 to 1000, preferably equal to 0 or 1, with $m+(m'*n)\geq 2$.

Preferably, $Z_1$ and $Z_2$ independently represent a reactive end group; more preferentially, $Z_1$ and $Z_2$ independently represent a group chosen from alkoxysilyl, hydroxysilyl, acetoxysilyl, vinylsilyl, acrylalkylsilyl, methacrylalkylsilyl, crotonylalkylsilyl, carboxyanhydridoalkylsilyl, carboxyalkylsilyl, hydroxyalkylsilyl, aldehydoalkylsilyl, mercaptoalkylsilyl, norbornenylsilyl, acylpentadienylalkylsilyl, maleimidoalkylsilyl, sulfonylalkylsilyl, (meth)acrylalkyl, crotonylalkyl, alkylepoxide such as propylepoxide or butylepoxide and azacyclopropane groups.

Such (poly)carbodiimide compounds are sold, for example, by the company Stahl B.V, under the name Permutex XR, or under the name RelcaLink10, under the name Picassian XL and Nisshinbo compounds sold under the name Carbodilite with the series V-02, V-02-L2, SV-02, E-02, V-10, SW-12G, E-03A, E-04DG-T, E-05, V-04, V-02B, V-04PF, V-05.

Preferably, the (poly)carbodiimide compound(s) are chosen from the compounds of formula (II) below:

(II)

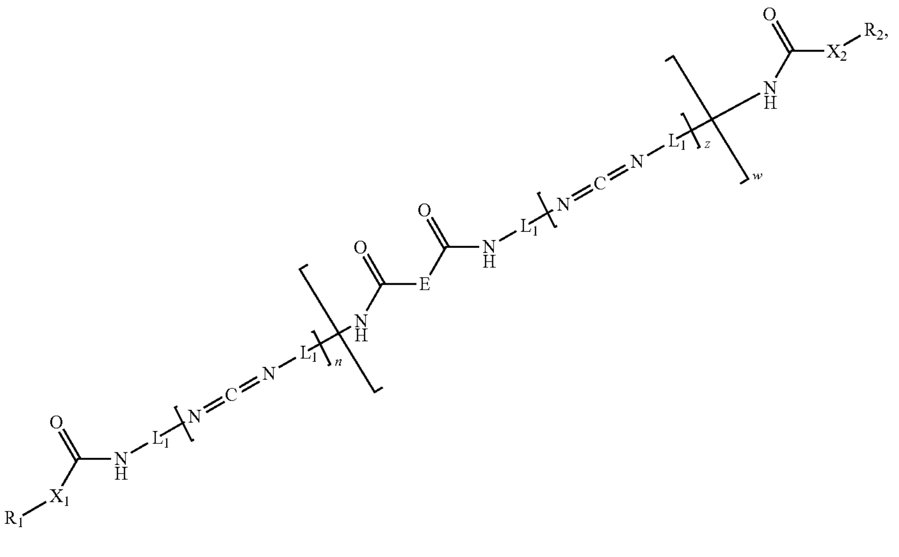

in which:

$X_1$ and $X_2$ independently represent an oxygen atom O, a sulfur atom S or an NH group;

$R_1$ and $R_2$ independently represent a hydrocarbon-based radical optionally interrupted with one or more heteroatoms;

n and z denote an integer ranging from 1 to 20, with $n+z\geq 2$ and w denotes an integer ranging from 1 to 3;

$L_1$ independently represents a $C_1$-$C_{18}$ divalent aliphatic hydrocarbon-based radical, a $C_3$-$C_{15}$ cycloalkylene radical, a $C_3$-$C_{12}$ heterocycloalkylene group or a $C_6$-$C_{14}$ arylene group, and mixtures thereof;

E independently represents a group chosen from: —O—$R_3$—O—; —S—$R_4$—S—; —$R_5$—N($R_6$)—$R_4$—N($R_6$)—$R_5$—;

in which $R_3$ and $R_4$ independently represent a divalent hydrocarbon-based radical optionally interrupted with one or more heteroatoms;

$R_5$ independently represents a covalent bond or a saturated divalent hydrocarbon-based radical, optionally interrupted with one or more heteroatoms;

$R_6$ independently represents a hydrogen atom or a hydrocarbon-based radical, optionally interrupted with one or more heteroatoms.

The term "hydrocarbon-based radical" means a saturated or unsaturated, linear or branched radical containing from 1 to 300 carbon atoms, preferably from 1 to 250 carbon atoms, more preferentially from 1 to 200 carbon atoms. Preferably, the hydrocarbon-based radical is a saturated linear radical.

The hydrocarbon-based radical may comprise one or more cyclic groups.

The hydrocarbon-based radical may be interrupted with one or more heteroatoms, in particular chosen from O, S or N and/or substituted with one or more cations, anions or zwitterions or cationic groups such as ammonium, anionic groups such as carboxylate, or zwitterionic groups, and/or comprising a metal ion which may be incorporated in the form of a salt.

The term "heteroatom(s)" means an oxygen O, sulfur S or nitrogen N atom, and also halogen atoms such as Cl, F, Br and I. If the heteroatom is included in the chain of the hydrocarbon-based radical, the heteroatom is preferably chosen from oxygen O, sulfur S or nitrogen N atoms.

Preferably, $X_1$ and $X_2$ independently represent an oxygen atom.

Preferably, $R_1$ and $R_2$ are independently chosen from dialkylamino alcohols, alkyl esters of hydroxycarboxylic acid and monoalkyl ethers of (poly)alkylene glycol, in which a hydroxyl group has been removed, and mixtures thereof.

In a preferred embodiment, $R_1$ and $R_2$ are independently chosen from groups (i) to (iv) below:

(i) the compound of formula (III) below:

$$R_7—O—C(O)—C(R_8)(H)— \quad (III),$$

in which $R_7$ represents a $C_1$-$C_3$alkyl group and $R_8$ represents a hydrogen atom or a $C_1$-$C_3$ alkyl group; preferably, $R_7$ is a methyl and $R_8$ is a hydrogen atom or a methyl.

(ii) the compound of formula (IV) below:

$$R_9—[O—CH_2—C(H)(R_{10})]_p— \quad (IV),$$

in which $R_9$ represents a $C_1$-$C_4$alkyl group, $R_{10}$ represents a hydrogen atom or a $C_1$-$C_4$ alkyl group and p denotes an integer ranging from 1 to 3; preferably, $R_9$ is a methyl, ethyl or butyl, $R_{10}$ is a hydrogen atom or a methyl and p is equal to 1.

(iii) the compound of formula (V) below:

$$(R_{11})_2N—CH_2—C(H)(R_{12})— \quad (V),$$

in which $R_{11}$ represents a $C_1$-$C_4$alkyl group and $R_{12}$ represents a hydrogen atom or a $C_1$-$C_4$ alkyl group; preferably, $R_{11}$ is a methyl, ethyl or butyl and $R_{12}$ is a hydrogen atom or a methyl.

(iv) the compound of formula (VI) below:

$$R_{13}—[O—CH_2—C(H)(R_{14})]_q— \quad (VI),$$

in which $R_{13}$ represents a $C_1$-$C_4$alkyl group or a phenyl, $R_{14}$ represents a hydrogen atom or a $C_1$-$C_4$ alkyl group and q denotes an integer ranging from 4 to 30; preferably, $R_{13}$ is a methyl, ethyl or butyl and $R_{14}$ is a hydrogen atom or a methyl.

Preferably, $R_1$ and $R_2$ independently represent a compound of formula (VI) in which $R_{13}$ represents a $C_1$-$C_4$ alkyl group or a phenyl, preferably a $C_1$-$C_4$ alkyl group, more preferentially a methyl, $R_{14}$ represents a hydrogen atom or a $C_1$-$C_4$ alkyl group, preferably a hydrogen atom and q denotes an integer ranging from 4 to 30.

According to an alternative embodiment, $R_1$ and $R_2$ are different and one of the radicals $R_1$ or $R_2$ represents a compound of formula (IV) as described above and the other radical $R_1$ or $R_2$ represents a compound of formula (VI) as described above.

Preferably, in formula (IV), $R_9$ is a methyl, ethyl or butyl and $R_{10}$ is a hydrogen atom or a methyl and p is equal to 1.

Preferably, in formula (VI), $R_{13}$ is a methyl, ethyl or butyl and $R_{14}$ is a hydrogen atom or a methyl and q denotes an integer ranging from 4 to 30.

According to another alternative embodiment, $R_1$ and $R_2$ are identical and represent a compound of formula (VI) in which $R_{13}$ represents a $C_1$-$C_4$ alkyl group or a phenyl, preferably a $C_1$-$C_4$ alkyl group, more preferentially a methyl, $R_{14}$ represents a hydrogen atom or a $C_1$-$C_4$ alkyl group, preferably a hydrogen atom and q denotes an integer ranging from 4 to 30.

Preferably, n denotes an integer ranging from 1 to 20, more preferentially from 2 to 20.

Preferably, z denotes an integer ranging from 1 to 20, more preferentially from 2 to 20.

Preferably, w is equal to 1.

Preferably, w is equal to 1, n+z denotes an integer ranging from 4 to 10.

Preferably, $L_1$ is chosen from a $C_1$-$C_{18}$ divalent aliphatic hydrocarbon-based radical such as methylene, ethylene and propylene, a $C_3$-$C_{15}$ cycloalkylene radical such as cyclopentylene, cycloheptylene and cyclohexylene, a $C_3$-$C_{12}$ heterocycloalkylene group such as imidazolene, pyrrolene and furanylene, or a $C_6$-$C_{14}$ arylene group such as phenylene, and mixtures thereof.

For example, $L_1$ may be chosen from a radical derived from tolylene diisocyanate, hexamethylene diisocyanate, xylylene diisocyanate, 2,2,4-trimethylhexamethylene diisocyanate, 1,12-dodecane diisocyanate, norbornane diisocyanate, 2,4-bis(8-isocyanatooctyl)-1,3-dioctylcyclobutane, 4,4'-dicyclohexylmethane diisocyanate, tetramethylxylylene diisocyanate, isophorone diisocyanate, 1,5-napththylene diisocyanate, 4,4'-diphenylmethane diisocyanate, 4,4'-diphenyldimethylmethane diisocyanate and phenylene diisocyanate, and mixtures thereof.

Preferably, $L_1$ is chosen from a $C_3$-$C_{15}$ cycloalkylene radical or a $C_6$-$C_{14}$ arylene group, and mixtures thereof, such as the compounds of formula (VII) below:

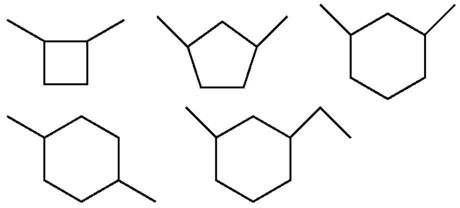

-continued

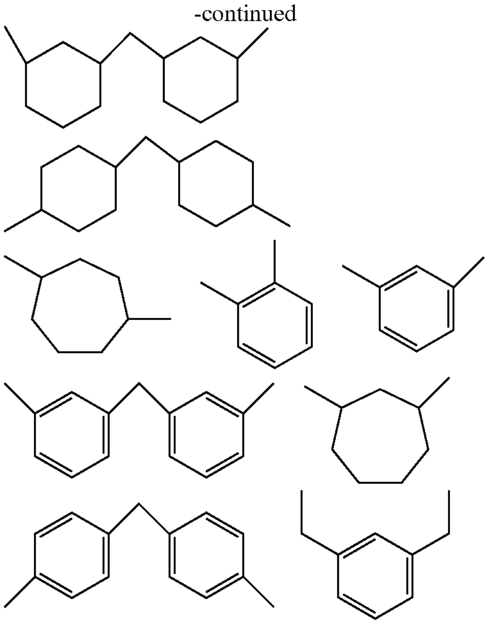

Preferably, $L_1$ is 4,4-dicyclohexylenemethane corresponding to formula (VIII) below:

(VIII)

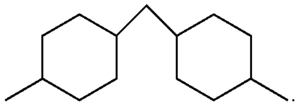

According to another embodiment, when L1 is a $C_6$-$C_{14}$ arylene group, $L_1$ is not the m-tetramethylxylylene radical represented by formula (IX) below:

(IX)

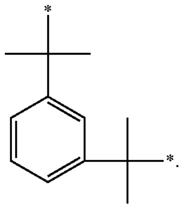

As indicated previously, E independently represents a group chosen from:

$—O—R_3—O—$; $—S—R_4—S—$; $—R_5—N(R_6)—R_4—N(R_6)—R_5—$;

in which $R_3$ and $R_4$ independently represent a divalent hydrocarbon-based radical optionally interrupted with one or more heteroatoms;

$R_5$ independently represents a covalent bond or a saturated divalent hydrocarbon-based radical, optionally interrupted with one or more heteroatoms; and $R_6$ independently represents a hydrogen atom or a hydrocarbon-based radical, optionally interrupted with one or more heteroatoms.

Preferably, $R_3$ and $R_4$ are independently chosen from a $C_6$-$C_{14}$ arylene radical such as phenylene, a $C_3$-$C_{12}$ cycloalkylene radical such as cyclopropylene and cyclobutylene, a linear or branched $C_1$-$C_{18}$ alkylene radical such as methylene and ethylene, optionally interrupted with one or more heteroatoms, and mixtures thereof.

More preferentially, $R_3$ and $R_4$ are independently chosen from a linear or branched $C_1$-$C_{18}$ alkylene radical such as methylene, butylene, propylene or ethylene, optionally interrupted with one or more heteroatoms.

Preferably, when $R_5$ is not a covalent bond, $R_5$ is chosen from a $C_6$-$C_{14}$ arylene radical such as phenylene, a $C_3$-$C_{12}$ cycloalkylene radical such as cyclopropylene and cyclobutylene, a linear or branched $C_1$-$C_{18}$ alkylene radical such as methylene and ethylene, optionally interrupted with one or more heteroatoms, and mixtures thereof.

Preferably, $R_6$ is chosen from a $C_6$-$C_{14}$ arylene radical such as phenylene, a $C_3$-$C_{12}$ cycloalkylene radical such as cyclopropylene and cyclobutylene, a linear or branched $C_1$-$C_{18}$ alkylene radical such as methylene and ethylene, optionally interrupted with one or more heteroatoms, and mixtures thereof.

Preferably, E represents a group $—O—R_3—O—$ in which $R_3$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof.

More preferentially, E represents a group $—O—R_3—O—$ in which $R_3$ represents a linear or branched $C_1$-$C_{18}$ alkylene radical such as methylene, butylene, propylene or ethylene, optionally interrupted with one or more heteroatoms.

According to a particular embodiment, the (poly)carbodiimide compound is a copolymer derived from α-methylstyryl isocyanates of formula (X) below:

(X)

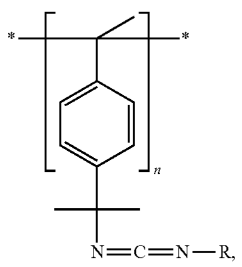

in which R independently represents an alkyl group containing from 1 to 24 carbon atoms, a cycloalkyl group containing from 3 to 24 carbon atoms or an aryl group containing from 6 to 24 carbon atoms, and n denotes an integer ranging from 2 to 100.

In this embodiment, the term "alkyl group" is as defined previously.

In this embodiment, the term "cycloalkyl group" is as defined previously.

In this embodiment, n may denote an integer ranging from 2 to 50, preferably from 3 to 30 and even more preferentially from 5 to 10.

According to another particular embodiment, the (poly) carbodiimide compound is a compound of formula (XI) below:

(XI)

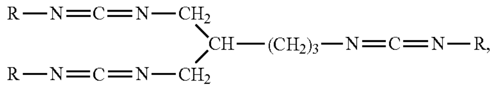

in which R independently represents an alkyl group containing from 1 to 24 carbon atoms, a cycloalkyl group containing from 3 to 24 carbon atoms or an aryl group containing from 6 to 24 carbon atoms.

The "alkyl group", the "cycloalkyl group" and the "aryl group" are as defined previously.

According to a preferred embodiment, the (poly)carbodiimide compound is chosen from the compounds of formula (I) or of formula (II) in which:

$X_1$ and $X_2$ independently represent an oxygen atom;

$R_1$ and $R_2$ are independently chosen from dialkylamino alcohols, alkyl esters of hydroxycarboxylic acid and monoalkyl ethers of (poly)alkylene glycol, in which a hydroxyl group has been removed, and mixtures thereof, preferably monoalkyl ethers of (poly)alkylene glycol, in which a hydroxyl group has been removed, more preferentially the compound of formula (VI) as described previously in which $R_{13}$ represents a $C_1$-$C_4$ alkyl group or a phenyl, preferably a $C_1$-$C_4$ alkyl group, more preferentially a methyl, $R_{14}$ represents a hydrogen atom or a $C_1$-$C_4$ alkyl group, preferably a hydrogen atom, and q denotes an integer ranging from 4 to 30;

n and z, when they are present, denote an integer ranging from 1 to 20, with n+z≥2 and w is equal to 1;

$L_1$, when it is present, is chosen from a $C_1$-$C_{18}$ divalent aliphatic hydrocarbon-based radical, a $C_3$-$C_{15}$ cycloalkylene radical, a $C_3$-$C_{12}$ heterocycloalkylene group or a $C_6$-$C_{14}$ arylene group, and mixtures thereof, preferably a $C_3$-$C_{15}$ cycloalkylene radical;

A, when it is present, is chosen from a $C_1$-$C_{18}$ divalent aliphatic hydrocarbon-based radical, a $C_3$-$C_{15}$ cycloalkylene radical, a $C_3$-$C_{12}$ heterocycloalkylene group or a $C_6$-$C_{14}$ arylene group, and mixtures thereof, preferably a $C_3$-$C_{15}$ cycloalkylene radical;

E, when it is present, independently represents a group chosen from:

$$—O—R_3—O—;\ —S—R_4—S—;\ —R_5—N(R_6)—R_4—N(R_6)—R_5—;$$

in which $R_3$ and $R_4$ are independently chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof, when $R_5$ is not a covalent bond, $R_5$, when it is present, is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof, and $R_6$, when it is present, is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof.

Preferably, the (poly)carbodiimide compound is chosen from the compounds of formula (II) in which:

$X_1$ and $X_2$ independently represent an oxygen atom;

$R_1$ and $R_2$ are independently chosen from dialkylamino alcohols, alkyl esters of hydroxycarboxylic acid and monoalkyl ethers of (poly)alkylene glycol, in which a hydroxyl group has been removed, and mixtures thereof, n and z denote an integer ranging from 1 to 20, with n+z≥2 and w is equal to 1;

$L_1$ is chosen from a $C_1$-$C_{18}$ divalent aliphatic hydrocarbon-based radical, a $C_3$-$C_{15}$ cycloalkylene radical, a $C_3$-$C_{12}$ heterocycloalkylene group or a $C_6$-$C_{14}$ arylene group, and mixtures thereof;

E independently represents a group chosen from:

$$—O—R_3—O—;\ —S—R_4—S—;\ —R_5—N(R_6)—R_4—N(R_6)—R_5—;$$

in which $R_3$ and $R_4$ are independently chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof, when $R_5$ is not a covalent bond, $R_5$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof, and $R_6$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof.

More preferentially, the (poly)carbodiimide compound is chosen from the compounds of formula (II) in which:

$X_1$ and $X_2$ independently represent an oxygen atom;

$R_1$ and $R_2$ are, independently, monoalkyl ethers of (poly) alkylene glycol, in which a hydroxyl group has been removed;

n and z denote an integer ranging from 1 to 20, with n+z≥2 and w is equal to 1;

$L_1$ is a $C_3$-$C_{15}$ cycloalkylene radical;

E independently represents a group chosen from:

$$—O—R_3—O—;\ —S—R_4—S—;\ —R_5—N(R_6)—R_4—N(R_6)—R_5—;$$

in which $R_3$ and $R_4$ are independently chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof, when $R_5$ is not a covalent bond, $R_5$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof, and $R_6$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof.

Even more preferentially, the (poly)carbodiimide compound is chosen from the compounds of formula (II) in which:

$X_1$ and $X_2$ independently represent an oxygen atom;

$R_1$ and $R_2$ independently represent the compound of formula (VI) below:

$$R_{13}—[O—CH_2—C(H)(R_{14})]_q— \quad (VI),$$

in which $R_{13}$ represents a $C_1$-$C_4$ alkyl group or a phenyl, preferably a $C_1$-$C_4$ alkyl group, more preferentially a methyl, $R_{14}$ represents a hydrogen atom or a $C_1$-$C_4$ alkyl group, preferably a hydrogen atom and q denotes an integer ranging from 4 to 30;

n and z denote an integer ranging from 2 to 20, with n+z ranging from 4 to 10 and w is equal to 1;

$L_1$ is a $C_3$-$C_{15}$ cycloalkylene radical such as cyclopentylene, cycloheptylene, cyclohexylene and 4,4-dicyclohexylenemethane; and E represents a group —O—$R_3$—O— in which $R_3$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof.

Even more preferentially, the (poly)carbodiimide compound is chosen from the compounds of formula (II) in which:

$X_1$ and $X_2$ independently represent an oxygen atom;

$R_1$ and $R_2$ independently represent the compound of formula (VI) below:

$$R_{13}—[O—CH_2—C(H)(R_{14})]_q— \quad (VI)$$

in which $R_{13}$ represents a $C_1$-$C_4$ alkyl group or a phenyl, preferably a $C_1$-$C_4$ alkyl group, more preferentially a methyl, $R_{14}$ represents a hydrogen atom or a $C_1$-$C_4$ alkyl group, preferably a hydrogen atom and q denotes an integer ranging from 4 to 30;

n and z denote an integer ranging from 1 to 20, preferably from 2 to 20, with n+z ranging from 4 to 10 and w is equal to 1;

$L_1$ is a $C_3$-$C_{15}$ cycloalkylene radical such as cyclopentylene, cycloheptylene, cyclohexylene and 4,4-dicyclohexylenemethane, preferably 4,4-dicyclohexylenemethane; and E represents a group —O—$R_3$—O— in which $R_3$ represents a linear or branched $C_1$-$C_{18}$ alkylene radical such as methylene, propylene, butylene or ethylene, optionally interrupted with one or more heteroatoms.

According to a preferred embodiment, the (poly)carbodiimide compound is a compound of formula (XII) below:

(XII)

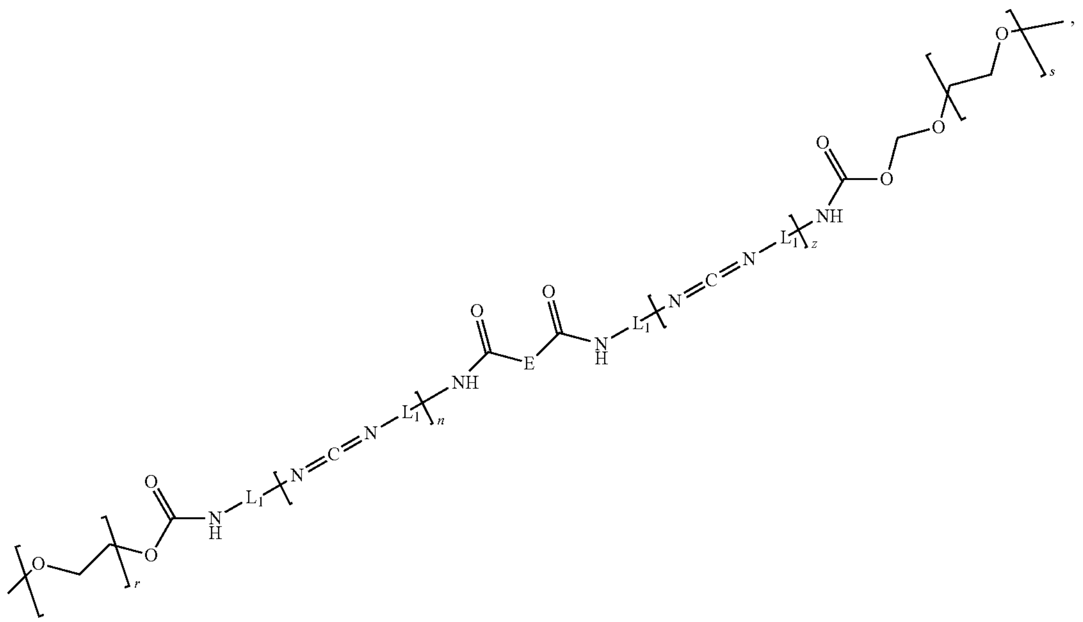

in which L1 is 4,4-dicyclohexylenemethane, n and z denote an integer ranging from 1 to 20, preferably from 2 to 20, with n+z ranging from 4 to 10, E represents a group —O—$R_3$—O— in which $R_3$ represents a linear or branched $C_1$-$C_{18}$ alkylene radical such as methylene, propylene, butylene or ethylene, optionally interrupted with one or more heteroatoms, and r and s denote an integer ranging from 4 to 30.

The total amount of the (poly)carbodiimide compound(s), present in composition A according to the invention, preferably ranges from 0.01% to 40% by weight, more preferentially from 0.1% to 30% by weight, better still from 0.5% to 25% by weight and even better still from 2% to 20% by weight relative to the total weight of composition A.

The total amount of the (poly)carbodiimide compound(s), present in composition C according to the invention, preferably ranges from 0.01% to 30% by weight, more preferentially from 0.1% to 25% by weight, better still from 0.2% to 20% by weight and even better still from 1% to 10% by weight relative to the total weight of composition C.

Non-Carboxylic Anionic Thickener

Composition A may also comprise a non-carboxylic anionic thickener.

For the purposes of the present invention, the term "non-carboxylic agent" means an agent which does not comprise any carboxylic acid functions (—COOH) or carboxylate functions (—$COO^-$).

For the purposes of the present invention, the term "thickener" means a compound which increases the viscosity of a composition into which it is introduced to a concentration of 0.05% by weight relative to the total weight of the composition, by at least 20 cps, preferably by at least 50 cps, at room temperature (25° C.), at atmospheric pressure and at a shear rate of 1 $s^{-1}$ (the viscosity may be measured using a cone/plate viscometer, a Haake R600 rheometer or the like).

Preferably, the non-carboxylic anionic thickener(s) are chosen from non-carboxylic anionic polymers, more preferentially from anionic polymers bearing (a) sulfonic group (s).

For the purposes of the invention, the term "anionic polymer" means a polymer comprising one or more anionic or anionizable groups, and not comprising any cationic or cationizable groups.

Advantageously, the non-carboxylic anionic thickener(s) are chosen from anionic polymers including at least one ethylenically unsaturated monomer bearing a sulfonic group, in free form or partially or totally neutralized form.

These polymers may be crosslinked or non-crosslinked. They are preferably crosslinked.

These polymers may be associative or non-associative, preferably non-associative.

It is recalled that "associative polymers" are polymers that are capable, in an aqueous medium, of reversibly associating with each other or with other molecules.

Their chemical structure more particularly comprises at least one hydrophilic zone and at least one hydrophobic zone.

The term "hydrophobic group" means a radical or polymer with a saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

The ethylenically unsaturated monomers bearing a sulfonic group are notably chosen from vinylsulfonic acid, styrenesulfonic acid, (meth)acrylamido($C_1$-$C_{22}$)alkylsulfonic acids, N—($C_1$-$C_{22}$)alkyl(meth)acrylamido($C_1$-$C_{22}$)alkylsulfonic acids such as undecylacrylamidomethanesulfonic acid, and also partially or totally neutralized forms thereof.

(Meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, will more preferentially be used.

2-Acrylamido-2-methylpropanesulfonic acid (AMPS), and also partially or totally neutralized forms thereof, will more particularly be used.

Among the 2-acrylamido-2-methylpropanesulfonic acid copolymers, mention may be made of partially or totally neutralized crosslinked copolymers of 2-acrylamido-2-methylpropanesulfonic acid and of acrylamide; mention may be made in particular of the product described in Example 1 of EP 503 853, and reference may be made to said document as regards these polymers.

Mention may also be made of copolymers of 2-acrylamido-2-methylpropanesulfonic acid or salts thereof and of hydroxyethyl acrylate, such as the compound sold under the name Sepinov EMT 10 by the company SEPPIC (INCI name: hydroxyethylacrylate/sodium acryloyldimethyl taurate copolymer).

The associative AMPS polymers may notably be chosen from statistical associative AMPS polymers modified by reaction with a $C_6$-$C_{22}$ n-monoalkylamine or di-n-alkylamine, and such as those described in patent application WO 00/31154 (forming an integral part of the content of the description). These polymers may also contain other ethylenically unsaturated hydrophilic monomers chosen, for example, from (meth)acrylic acid derivatives, such as esters thereof obtained with monoalcohols or mono- or polyalkylene glycols, (meth)acrylamides, vinylpyrrolidone, or mixtures of these compounds.

The preferred polymers of this family are chosen from associative copolymers of AMPS and of at least one ethylenically unsaturated hydrophobic monomer.

These same copolymers may also contain one or more ethylenically unsaturated monomers not including a fatty chain, such as (meth)acrylic acid derivatives, notably esters thereof obtained with monoalcohols or mono- or polyalkylene glycols, (meth)acrylamides, vinylpyrrolidone, or mixtures of these compounds.

These copolymers are described notably in patent application EP-A 750 899, U.S. Pat. No. 5,089,578 and in the following publications from Yotaro Morishima:

- Self-assembling amphiphilic polyelectrolytes and their nanostructures, *Chinese Journal of Polymer Science*, Vol. 18, No. 40, (2000), 323-336;
- Micelle formation of random copolymers of sodium 2-(acrylamido)-2-methylpropanesulfonate and a nonionic surfactant macromonomer in water as studied by fluorescence and dynamic light scattering, *Macromolecules*, Vol. 33, No. 10, (2000), 3694-3704;
- Solution properties of micelle networks formed by nonionic moieties covalently bound to an polyelectrolyte: salt effects on rheological behavior—*Langmuir*, Vol. 16, No. 12, (2000) 5324-5332;
- Stimuli responsive amphiphilic copolymers of sodium 2-(acrylamido)-2-methylpropanesulfonate and associative macromonomers—*Polym. Preprint, Div. Polym. Chem.* 40(2), (1999), 220-221.

Among these polymers, mention may be made of:

- crosslinked or non-crosslinked, neutralized or non-neutralized copolymers, including from 15% to 60% by weight of AMPS units and from 40% to 85% by weight of ($C_5$-$C_{16}$)alkyl(meth)acrylamide or ($C_5$-$C_{16}$)alkyl (meth)acrylate units relative to the polymer, such as those described in patent application EP-A750 899;
- terpolymers including from 10 mol % to 90 mol % of acrylamide units, from 0.1 mol % to 10 mol % of AMPS units and from 5 mol % to 80 mol % of n-($C_6$-$C_{18}$)alkylacrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Preferably, the non-carboxylic anionic thickener(s) are chosen from sodium 2-acrylamido-2-methylpropanesulfonate/hydroxyethyl acrylate copolymer, sold by the company SEPPIC (INCI name hydroxyethyl acrylate/sodium acryloyldimethyl taurate copolymer).

Advantageously, the total amount of the non-carboxylic anionic thickener(s) ranges from 0.01% to 20% by weight, preferably from 0.1% to 10% by weight, better still from 0.1% to 5% by weight, and even better still from 0.1% to 2% by weight, relative to the total weight of composition A.

Composition B

As indicated previously, the colouring process according to the invention uses a composition B as defined above.

Associative Polymers

Composition B according to the invention used in the context of the colouring process according to the invention comprises at least one associative polymer.

The associative polymers are different from the non-carboxylic anionic thickeners described previously.

It is recalled that "associative polymers" are polymers that are capable, in an aqueous medium, of reversibly associating with each other or with other molecules.

Their chemical structure more particularly comprises at least one hydrophilic zone and at least one hydrophobic zone.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

The associative polymers may be of nonionic, anionic, cationic or amphoteric nature.

Preferably, the associative polymer(s) are chosen from anionic associative polymers.

Among the associative polymers of anionic type that may be mentioned are:

(a) those including at least one hydrophilic unit and at least one fatty-chain allyl ether unit, more particularly those whose hydrophilic unit is formed by an ethylenic unsaturated anionic monomer, more particularly a vinylcarboxylic acid and most particularly an acrylic acid or a methacrylic acid or mixtures thereof.

Among these anionic associative polymers, the ones that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether, and from 0 to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), notably those sold by the company Ciba under the names Salcare SC 80® and Salcare SC 90®, which are aqueous 30% emulsions of a crosslinked terpolymer of methacrylic acid, of ethyl acrylate and of steareth-10 allyl ether (40/50/10);

(b) those including i) at least one hydrophilic unit of unsaturated olefinic carboxylic acid type, and ii) at least one hydrophobic unit of the type such as a ($C_{10}$-$C_{30}$) alkyl ester of an unsaturated carboxylic acid.

($C_{10}$-$C_{30}$) Alkyl esters of unsaturated carboxylic acids that are useful in the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Among the anionic associative polymers of this type that will be used more particularly are those constituted of from 95% to 60% by weight of acrylic acid (hydrophilic unit), 4% to 40% by weight of $C_{10}$-$C_{30}$ alkyl acrylate (hydrophobic unit) and 0 to 6% by weight of crosslinking polymerizable monomer, or alternatively those constituted of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described previously.

Among said polymers above, the ones most particularly preferred according to the present invention are the products sold by the company Goodrich under the trade names Pemulen TR1®, Pemulen TR2®, Carbopol 1382®, and even more preferentially Pemulen TR1®, and the product sold by the company SEPPIC under the name Coatex SX®.

Mention may also be made of the acrylic acid/lauryl methacrylate/vinylpyrrolidone terpolymer sold under the name Acrylidone LM by the company ISP.

(c) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies.

(d) acrylic terpolymers comprising:

i) about 20% to 70% by weight of an α,β-monoethylenically unsaturated carboxylic acid [A], ii) about 20% to 80% by weight of an α,β-monoethylenically unsaturated non-surfactant monomer other than [A], iii) about 0.5% to 60% by weight of a nonionic monourethane which is the product of reaction of a monohydric surfactant with a monoethylenically unsaturated monoisocyanate, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion.

(e) copolymers including among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

An example of a compound of this type that may be mentioned is Aculyn 22® sold by the company Röhm & Haas, which is a methacrylic acid/ethyl acrylate/oxyalkylenated stearyl methacrylate terpolymer; and also Aculyn 88, also sold by the company Röhm & Haas.

Advantageously, the associative polymer(s) are chosen from acrylic associative polymers, more preferentially carboxylic acrylic associative polymers.

Particularly preferably, the associative polymer(s) different from the non-carboxylic anionic thickeners are chosen from copolymers including among their monomers an α,β-monoethylenically unsaturated carboxylic acid and an ester of an α,β-monoethylenically unsaturated carboxylic acid and of an oxyalkylenated fatty alcohol.

Advantageously, the total amount of the associative polymer(s) ranges from 0.1% to 30% by weight, preferably from 0.1% to 20% by weight, more preferentially from 0.2% to 10% by weight, better still from 0.2% to 5% by weight and even more particularly from 0.2% to 2% by weight, relative to the total weight of composition B.

Advantageously, the total amount of the associative polymer(s) ranges from 0.05% to 15% by weight, preferably from 0.05% to 10% by weight, more preferentially from 0.1% to 5% by weight and even more preferentially from 0.1% to 1% by weight, relative to the total weight of composition C.

Compound Containing at Least One Carboxylic Acid Group

Composition B according to the invention used in the context of the colouring process according to the invention comprises at least one compound, different from the associative polymers, containing at least one carboxylic acid group.

Preferably, the compound, different from the associative polymers, containing at least one carboxylic acid group is chosen from silicone compounds comprising at least one carboxylic group, polyurethanes, acrylic polymers and mixtures thereof.

Polyurethanes and Acrylic Polymers:

According to a preferred embodiment, composition B comprises one or more compounds, different from the associative polymers, containing at least one carboxylic acid group chosen from polyurethanes, acrylic polymers and mixtures thereof.

Preferably, the compound(s), different from the associative polymers, containing at least one carboxylic acid group are in the form of aqueous dispersions of particles of polymer(s) chosen from polyurethanes, acrylic polymers and mixtures thereof.

Preferably, composition B comprises one or more compounds, different from the associative polymers, containing at least one carboxylic acid group in the form of aqueous dispersions of particles of polyurethanes, acrylic polymers and mixtures thereof.

Thus, in this embodiment, the polymer(s) used in the aqueous dispersions of polymer particles are different from the associative polymers.

The dispersion(s) may be simple dispersions in the aqueous medium of the cosmetic composition. As a particular case of dispersions, mention may be made of latexes.

The aqueous dispersion(s) of polymer particles may be chosen from aqueous dispersions of polyurethane particles.

More particularly, the polyurethane(s) present in the aqueous dispersions used in the present invention are derived from the reaction of:

a prepolymer of formula (A) below:

(A)

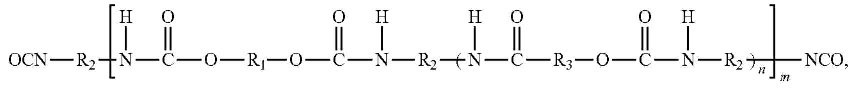

in which:

- $R_1$ represents a divalent radical of a dihydroxylated compound;
- $R_2$ represents a radical of an aliphatic or cycloaliphatic polyisocyanate;
- $R_3$ represents a radical of a low molecular weight diol, optionally substituted with one or more ionic groups;
- n represents an integer ranging from 1 to 5, and
- m is greater than 1;
  - at least one chain extender according to formula (B) below:

$$H_2N—R_4—NH_2 \quad (B),$$

in which $R_4$ represents an alkylene or alkylene oxide radical which is not substituted with one or more ionic or potentially ionic groups; and

- at least one chain extender according to formula (C) below:

$$H_2N—R_5—NH_2 \quad (C),$$

in which $R_5$ represents an alkylene radical substituted with one or more ionic or potentially ionic groups.

Among the dihydroxylated compounds that may be used according to the present invention, mention may be made notably of the compounds containing two hydroxyl groups and having a number-average molecular weight from about 700 to about 16 000, and preferably from about 750 to about 5000. As examples of dihydroxylated compounds of high molecular weight, mention may be made of polyol polyesters, polyol polyethers, polyhydroxylated polycarbonates, polyhydroxylated polyacetates, polyhydroxylated polyacrylates, polyhydroxylated amide polyesters, polyhydroxylated polyalkadienes, polyhydroxylated polythioethers, and mixtures thereof. Preferably, the hydroxylated compounds are chosen from polyol polyesters, polyol polyethers, polyhydroxylated polycarbonates, and mixtures thereof.

The polyisocyanates that may be used according to the present invention are notably chosen from organic diisocyanates with a molecular weight of about 112 to 1000, and preferably about 140 to 400.

Preferably, the polyisocyanates are chosen from diisocyanates and more particularly from those represented by the general formula $R_2(NCO)_2$, in which $R_2$ represents a divalent aliphatic hydrocarbon-based group containing from 4 to 18 carbon atoms, a divalent cycloaliphatic hydrocarbon-based group containing from 5 to 15 carbon atoms, a divalent araliphatic hydrocarbon-based group containing from 7 to 15 carbon atoms or a divalent aromatic hydrocarbon-based group containing from 6 to 15 carbon atoms.

Preferably, $R_2$ represents an organic diisocyanate. As examples of organic diisocyanates, the following may notably be chosen: tetramethylene diisocyanate, 1,6-hexamethylene diisocyanate, dodecamethylene diisocyanate, 1,3-diisocyanatocyclohexane, 1,4-diisocyanatocyclohexane, 3-isocyanatomethyl-3,5,5-trimethylcyclohexane isocyanate (isophorone diisocyanate or IPDI), bis(4-isocyanatocyclohexyl)methane, 1,3-bis(isocyanatomethyl)cyclohexane, 1,4-bis(isocyanatomethyl)cyclohexane, bis(4-isocyanato-3-methyl-cyclohexyl)methane, isomers of toluene diisocyanate (TDI) such as toluene 2,4-diisocyanate, toluene 2,6-diisocyanate and mixtures thereof, hydrogenated toluene diisocyanate, diphenylmethane 4,4'-diisocyanate and mixtures with its diphenylmethane 2,4-diisocyanate isomers and optionally diphenylmethane 2,2'-diisocyanate isomers, naphthalene 1,5-diisocyanate, and mixtures thereof.

Preferably, the diisocyanates are aliphatic and cycloaliphatic diisocyanates, and are more preferentially chosen from 1,6-hexamethylene diisocyanate, 3-isocyanatomethyl-3,5,5-trimethylcyclohexane isocyanate, and mixtures thereof.

According to the present invention, the term "low molecular weight diol" refers to a diol with a molecular weight from about 62 to 700, and preferably from 62 to 200. These diols may comprise aliphatic, alicyclic or aromatic groups. Preferably, they comprise only aliphatic groups.

Preferably, $R_3$ represents a low molecular weight diol containing more than 20 carbon atoms, more preferentially chosen from ethylene glycol, diethylene glycol, 1,2-propanediol, 1,3-propanediol, 1,4-butanediol, 1,3-butylene glycol, neopentyl glycol, butylethylpropanediol, cyclohexanediol, 1,4-cyclohexanedimethanol, 1,6-hexanediol, bisphenol A (2,2-bis(4-hydroxyphenyl)propane), hydrogenated bisphenol A (2,2-bis(4-hydroxycyclohexyl)propane), and mixtures thereof.

The low molecular weight diols may optionally comprise ionic or potentially ionic groups. Examples of low molecular weight diols containing ionic or potentially ionic groups are notably described in U.S. Pat. No. 3,412,054. Such compounds are preferably chosen from dimethylolbutanoic acid, dimethylolpropionic acid, polycaprolactone diols containing a carboxyl group, and mixtures thereof.

If low molecular weight diols containing ionic or potentially ionic groups are used, they are preferably used in an amount such that less than 0.30 meq of COOH per gram of polyurethane is present in the polyurethane dispersion.

The prepolymer is extended by means of two families of chain extenders. The first family of chain extenders corresponds to the compounds of general formula (B).

The chain extenders of formula (B) are preferably chosen from alkylenediamines, such as hydrazine, ethylenediamine, propylenediamine, 1,4-butylenediamine, piperazine; alkylene oxide diamines, such as 3-{2-[2-(3-aminopropoxy) ethoxy]ethoxy}propylamine (also known as dipropylamine diethylene glycol or DPA-DEG available from Tomah Products, Milton, Wis.), 2-methyl-1,5-pentanediamine (Dytec A from DuPont), hexanediamine, isophorone diamine, 4,4-methylenedi(cyclohexylamine), ether-amines of the DPA series, available from Tomah Products, Milton, Wis., such as dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol; and mixtures thereof.

The second family of chain extenders corresponds to the compounds of general formula (C). Such compounds preferably have an ionic or potentially ionic group and two groups that can react with isocyanate groups. Such compounds may optionally comprise two groups that react with isocyanate groups and one group which is ionic or capable of forming an ionic group.

The ionic or potentially ionic group may preferably be chosen from ternary or quaternary ammonium groups or groups that can be converted into such groups, a carboxyl group, a carboxylate group, a sulfonic acid group and a sulfonate group. The at least partial conversion of groups that can be converted into a ternary or quaternary ammonium group salt may be performed before or during the mixing with water.

The chain extenders of formula (C) are preferably chosen from diaminosulfonates, for instance the sodium salt of N-(2-aminoethyl)-2-aminoethanesulfonic acid (ASA), the sodium salt of N-(2-aminoethyl)-2-aminopropionic acid, and mixtures thereof.

The polyurethane that may be used according to the present invention may optionally also comprise compounds which are located, respectively, at the chain ends and terminate said chains (chain terminators). Such compounds are notably described in U.S. Pat. Nos. 7,445,770 and/or 7,452,770.

Preferably, the aqueous dispersion of polyurethane particles has a viscosity of less than 2000 mPa·s at 23° C., more preferentially less than 1500 and better still less than 1000. Even more preferably, the aqueous polyurethane dispersion has a glass transition temperature of less than 0° C.

Preferably also, the aqueous polyurethane dispersion has a polyurethane (or active material, or solids) content, on the basis of the weight of the dispersion, of from 20% to 60% by weight, more preferentially from 25% to 55% by weight and even better still from 30% to 50% by weight. This means that the polyurethane content (solids) of the aqueous dispersion is preferably from 20% to 60% by weight, more preferentially from 25% to 55% by weight and better still from 30% to 50% by weight, relative to the total weight of the dispersion.

Preferably also, the aqueous dispersion of polyurethane particles has a glass transition temperature (Tg) of less than or equal to −25° C., preferably less than −35° C. and more preferentially less than −40° C.

The polyurethane particles may have a mean diameter ranging up to about 1000 nm, for example from about 50 nm to about 800 nm, better still from about 100 nm to about 500 nm. These particle sizes may be measured with a laser particle size analyzer (for example Brookhaven BI90).

As non-limiting examples of aqueous polyurethane dispersions, mention may be made of those sold under the name Baycusan® by Bayer, for instance Baycusan® C1000 (INCI name: polyurethane-34), Baycusan® C1001 (INCI name: polyurethane-34), Baycusan® C1003 (INCI name: polyurethane-32), Baycusan® C1004 (INCI name: polyurethane-35) and Baycusan® C1008 (INCI name: polyurethane-48).

Mention may also be made of the aqueous polyurethane dispersions of isophthalic acid/adipic acid copolymer/hexylene glycol/neopentyl glycol/dimethylol acid/isophorone diisocyanate (INCI name: Polyurethane-1, such as Luviset® PUR, BASF), the polyurethane of polycarbonate, polyurethane and aliphatic polyurethane of aliphatic polyester (such as the Neorez® series, DSM, such as Neorez® R989, Neorez® and R-2202).

According to a preferred embodiment, the aqueous dispersion of polyurethane particles may be chosen from aqueous dispersions of particles of compounds having the INCI name polyurethane-35 or compounds having the INCI name polyurethane-34.

Preferably, the compound(s), different from the associative polymers, containing at least one carboxylic acid group are in the form of aqueous dispersions of particles of acrylic polymers, more preferentially in the form of aqueous dispersions of film-forming acrylic polymer particles.

For the purposes of the invention, the term "polymer" means a compound corresponding to the repetition of one or more units (these units being derived from compounds known as monomers). This or these unit(s) are repeated at least twice and preferably at least three times.

The term "film-forming polymer" refers to a polymer that is capable of forming, by itself or in the presence of an auxiliary film-forming agent, a macroscopically continuous film on a support, notably on keratinous materials, and preferably a cohesive film.

For the purposes of the present invention, the term "acrylic polymer" means a polymer synthesized from at least one monomer chosen from (meth)acrylic acid and/or (meth)acrylic acid ester and/or (meth)acrylic acid amide.

The unit(s) derived from the (meth)acrylic acid monomers of the polymer may optionally be in the form of salt(s), notably of alkali metal, alkaline-earth metal or ammonium salt(s), or organic base salt(s).

The (meth)acrylic acid esters (also known as (meth) acrylates) are advantageously chosen from alkyl (meth) acrylates, in particular $C_1$ to $C_{30}$, preferably $C_1$ to $C_{20}$ and better still $C_1$ to $C_{10}$ alkyl (meth)acrylates, aryl (meth) acrylates, in particular $C_6$ to $C_{10}$ aryl (meth)acrylates, and hydroxyalkyl (meth)acrylates, in particular $C_2$ to $C_6$ hydroxyalkyl (meth)acrylates.

Among the alkyl (meth)acrylates that may be mentioned are methyl (meth)acrylate, ethyl (meth)acrylate, butyl (meth)acrylate, isobutyl (meth)acrylate, 2-ethylhexyl (meth) acrylate, lauryl (meth)acrylate and cyclohexyl (meth)acrylate.

Among the hydroxyalkyl (meth)acrylates that may be mentioned are hydroxyethyl acrylate, 2-hydroxypropyl acrylate, hydroxyethyl methacrylate and 2-hydroxypropyl methacrylate.

Among the aryl (meth)acrylates that may be mentioned are benzyl acrylate and phenyl acrylate.

The (meth)acrylic acid esters that are particularly preferred are alkyl, preferably $C_1$ to $C_{30}$, more preferentially $C_1$ to $C_{20}$, even better still $C_1$ to $C_{10}$, and even more particularly $C_1$ to $C_4$, alkyl (meth)acrylates.

According to the present invention, the alkyl group of the esters may be fluorinated, or even perfluorinated, i.e. some or all of the hydrogen atoms of the alkyl group are substituted with fluorine atoms.

As (meth)acrylic acid amides, examples that may be mentioned include (meth)acrylamides and also N-alkyl (meth)acrylamides, in particular N—($C_2$ to $C_{12}$ alkyl)(meth) acrylamides. Among the N-alkyl(meth)acrylamides that may be mentioned are N-ethylacrylamide, N-t-butylacrylamide, N-t-octylacrylamide and N-undecylacrylamide.

The acrylic polymer according to the invention may be a homopolymer or a copolymer, advantageously a copolymer, better still a copolymer of (meth)acrylic acid and of (meth) acrylic acid esters.

Preferably, the acrylic polymer(s) according to the invention comprise one or more units derived from the following monomers:

a) (meth)acrylic acid; and b) $C_1$ to $C_{30}$, more preferentially $C_1$ to $C_{20}$, better still $C_1$ to $C_{10}$, and even more particularly $C_1$ to $C_4$, alkyl (meth)acrylate.

Preferably, the aqueous dispersion of acrylic polymer particles does not comprise any surfactant.

The term "surfactant" refers to any agent that is capable of modifying the surface tension between two surfaces.

Among the acrylic polymers according to the invention, mention may be made of copolymers of (meth)acrylic acid and of methyl or ethyl (meth)acrylate, in particular copolymers of methacrylic acid and of ethyl acrylate such as the compound sold under the trade name Luvimer MAE by the company BASF, or the compound Polyacrylate-2 Crosspolymer sold under the trade name Fixate Superhold Polymer by the company Lubrizol, or the compound Acrylate Copolymer sold under the trade name Daitosol 3000VP3 by the company Daito Kasei Kogyo, or the compound Acrylate Polymer sold under the trade name Daitosol 3000 SLPN-PE1 by the company Daito Kasei Kogyo.

The acrylic polymer may optionally comprise one or more additional monomers, other than the (meth)acrylic acid and/or (meth)acrylic acid ester and/or (meth)acrylic acid amide monomers.

By way of additional monomer, mention will be made, for example, of styrene monomers, in particular styrene and α-methylstyrene, and preferably styrene.

In particular, the acrylic polymer may be a styrene/(meth) acrylate copolymer and notably a polymer chosen from copolymers resulting from the polymerization of at least one styrene monomer and at least one $C_1$ to $C_{20}$, preferably $C_1$ to $C_{10}$, alkyl (meth)acrylate monomer.

The $C_1$ to $C_{10}$ alkyl (meth)acrylate monomer may be chosen from methyl acrylate, ethyl acrylate, propyl acrylate, butyl acrylate, hexyl acrylate, octyl acrylate and 2-ethylhexyl acrylate.

As acrylic polymer, mention may be made of the styrene/(meth)acrylate copolymers sold under the name Joncryl 77 by the company BASF, under the name Yodosol GH41F by the company Akzo Nobel and under the name Syntran 5760 CG by the company Interpolymer.

Preferably, composition B comprises at least one aqueous dispersion of acrylic polymer particles.

More preferentially, composition B comprises at least one aqueous dispersion of acrylic polymer particles comprising one or more units derived from the following monomers:

a) (meth)acrylic acid; and b) $C_1$ to $C_{30}$, more preferentially $C_1$ to $C_{20}$, better still $C_1$ to $C_{10}$, and even more particularly $C_1$ to $C_4$, alkyl (meth)acrylate.

Preferably, the aqueous dispersion of acrylic polymer particles has an acrylic polymer (or active material, or solids) content, on the basis of the weight of the dispersion, of from 20% to 60% by weight, more preferentially from 22% to 55% by weight and better still from 25% to 50% by weight.

The total amount of the compound(s), different from the associative polymers, containing at least one carboxylic acid group present in composition B, preferably ranges from 0.2% to 60% by weight, more preferentially from 1% to 55% by weight, better still from 5% to 50% by weight, and even more preferentially from 10% to 45% by weight, relative to the total weight of composition B.

The total amount of the compound(s), different from the associative polymers, containing at least one carboxylic acid group preferably ranges from 0.1% to 35% by weight, more preferentially from 0.5% to 30% by weight, better still from 1% to 25% by weight, and even more preferentially from 3% to 25% by weight, relative to the total weight of composition C.

The total amount of the aqueous dispersion(s) of polymer particles, different from the associative polymer(s) as described previously, chosen from polyurethanes, acrylic polymers, and mixtures thereof, preferably ranges from 0.2% to 60% by weight, more preferentially from 1% to 55% by weight, better still from 5% to 50% by weight, and even more preferentially from 10% to 45% by weight, relative to the total weight of composition B.

According to a particular embodiment, the total amount of the aqueous dispersion(s) of acrylic polymer particles, different from the associative polymer(s) as described previously, preferably ranges from 0.2% to 60% by weight, more preferentially from 1% to 55% by weight, better still from 5% to 50% by weight, and even more preferentially from 10% to 45% by weight, relative to the total weight of composition B.

The total amount of the aqueous dispersion(s) of polymer particles, different from the associative polymer(s) as described previously, chosen from polyurethanes, acrylic polymers, and mixtures thereof, preferably ranges from 0.1% to 35% by weight, more preferentially from 0.5% to 30% by weight, better still from 1% to 25% by weight, and even more preferentially from 3% to 25% by weight, relative to the total weight of composition C.

According to a particular embodiment, the total amount of the aqueous dispersion(s) of acrylic polymer particles, different from the associative polymer(s) as described previously, preferably ranges from 0.1% to 35% by weight, more preferentially from 0.5% to 30% by weight, better still from 1% to 25% by weight, and even more preferentially from 3% to 25% by weight, relative to the total weight of composition C.

Compound Containing at Least One Hydroxyl Function

Composition B according to the invention used in the context of the colouring process according to the invention comprises at least one compound containing at least one hydroxyl function.

Advantageously, said compound containing at least one hydroxyl function is aromatic or non-aromatic.

Preferably, the compound containing at least one hydroxyl function is chosen from those with a molecular weight of less than 500 g/mol, more preferentially less than 300 g/mol, better still less than 250 g/mol.

Preferably, said composition B comprises at least two compounds containing at least one hydroxyl function.

According to a particular embodiment, when said composition B comprises at least two compounds containing at least one hydroxyl function, at least one is an aromatic compound, and at least one is a non-aromatic compound.

According to a particular embodiment, said composition B comprises at least three compounds containing at least one hydroxyl function.

Preferably, composition B comprises at least one compound, preferably at least two compounds, containing at least one hydroxyl function, chosen from phenoxyethanol, 1,2-hexanediol, 4-hydroxyacetophenone, ethanol, chlorphenesin, pentylene glycol and mixtures thereof.

According to a particular embodiment, composition B comprises at least three compounds, preferably at least four compounds, containing at least one hydroxyl function, chosen from phenoxyethanol, 1,2-hexanediol, 4-hydroxyacetophenone, ethanol, chlorphenesin, pentylene glycol and mixtures thereof.

According to a particularly preferred embodiment, said compound containing at least one hydroxyl function is chosen from a mixture of phenoxyethanol, 1,2-hexanediol, 4-hydroxyacetophenone, ethanol, chlorphenesin and pentylene glycol.

According to another embodiment, composition B comprises at least 1,2-hexanediol, preferably in a content ranging from 0.1% to 2% by weight, more preferentially ranging from 0.5% to 1.5% by weight, relative to the total weight of composition B.

Advantageously, the total content of compound(s) containing at least one hydroxyl function is at least 2% by weight, preferably at least 3% by weight, more preferentially from 3% to 30% by weight, even more preferentially from 4% to 20% by weight and better still from 5% to 15% by weight relative to the total weight of composition B.

Colouring Agent

Composition A and/or composition B according to the invention used in the context of the colouring process according to the invention comprises at least one colouring agent chosen from pigments, direct dyes and mixtures thereof.

Preferably, composition B comprises at least one colouring agent chosen from pigments, direct dyes and their mixtures.

Advantageously, composition A and/or composition B according to the invention used in the context of the colouring process according to the invention comprises one or more pigments.

Preferably, composition B according to the invention comprises one or more pigments.

The term "pigment" refers to any pigment that gives colour to keratinous materials. Their solubility in water at 25° C. and at atmospheric pressure (760 mmHg) is less than 0.05% by weight, and preferably less than 0.01%.

The pigments that may be used are notably chosen from the organic and/or mineral pigments known in the art, notably those described in Kirk-Othmer's *Encyclopedia of Chemical Technology* and in *Ullmann's Encyclopedia of Industrial Chemistry*.

They may be natural, of natural origin, or non-natural.

These pigments may be in pigment powder or paste form. They may be coated or uncoated.

The pigments may be chosen, for example, from mineral pigments, organic pigments, lakes, pigments with special effects such as nacres or glitter flakes, and mixtures thereof.

The pigment may be a mineral pigment. The term "mineral pigment" refers to any pigment that satisfies the definition in Ullmann's encyclopedia in the chapter on inorganic pigments. Among the mineral pigments that are useful in the present invention, mention may be made of iron oxides, chromium oxides, manganese violet, ultramarine blue, chromium hydrate, ferric blue and titanium oxide.

The pigment may be an organic pigment. The term "organic pigment" refers to any pigment that satisfies the definition in Ullmann's encyclopedia in the chapter on organic pigments.

The organic pigment may notably be chosen from nitroso, nitro, azo, xanthene, pyrene, quinoleine, quinoline, anthraquinone, triphenylmethane, fluorane, phthalocyanine, metal-complex, isoindolinone, isoindoline, quinacridone, perinone, perylene, diketopyrrolopyrrole, indigo, thioindigo, dioxazine, triphenylmethane and quinophthalone compounds.

In particular, the white or coloured organic pigments may be chosen from carmine, carbon black, aniline black, azo yellow, quinacridone, phthalocyanine blue, the blue pigments codified in the Color Index under the references CI 42090, 69800, 69825, 74100, 74160, the yellow pigments codified in the Color Index under the references CI 11680, 11710, 19140, 20040, 21100, 21108, 47000, 47005, the green pigments codified in the Color Index under the references CI 61565, 61570, 74260, the orange pigments codified in the Color Index under the references CI 11725, 45370, 71105, the red pigments codified in the Color Index under the references CI 12085, 12120, 12370, 12420, 12490, 14700, 15525, 15580, 15620, 15630, 15800, 15850, 15865, 15880, 26100, 45380, 45410, 58000, 73360, 73915, 75470, the pigments obtained by oxidative polymerization of indole or phenol derivatives as described in patent FR 2 679 771.

Examples that may also be mentioned include pigment pastes of organic pigments, such as the products sold by the company Hoechst under the names:

Cosmenyl Yellow 10G: Yellow 3 pigment (CI 11710);
Cosmenyl Yellow G: Yellow 1 pigment (CI 11680);
Cosmenyl Orange GR: Orange 43 pigment (CI 71105);
Cosmenyl Red R: Red 4 pigment (CI 12085);
Cosmenyl Carmine FB: Red 5 pigment (CI 12490);
Cosmenyl Violet RL: Violet 23 pigment (CI 51319);
Cosmenyl Blue A2R: Blue 15.1 pigment (CI 74160);
Cosmenyl Green GG: Green 7 pigment (CI 74260);
Cosmenyl Black R: Black 7 pigment (CI 77266).

The pigments in accordance with the invention may also be in the form of composite pigments, as described in patent EP 1 184 426. These composite pigments may be composed notably of particles including a mineral core, at least one binder for attaching the organic pigments to the core, and at least one organic pigment which at least partially covers the core.

The organic pigment may also be a lake. The term "lake" refers to dyes adsorbed onto insoluble particles, the assembly thus obtained remaining insoluble during use.

The mineral substrates onto which the dyes are adsorbed are, for example, alumina, silica, calcium sodium borosilicate or calcium aluminium borosilicate and aluminium.

Among the dyes, mention may be made of carminic acid. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green 5 (CI 61 570), D&C Yellow 10 (CI 77 002), D&C Green 3 (CI 42 053), D&C Blue 1 (CI 42 090).

An example of a lake that may be mentioned is the product known under the following name: D&C Red 7 (CI 15 850:1).

The pigment may also be a pigment with special effects. The term "pigments with special effects" means pigments that generally create a coloured appearance (characterized by a certain shade, a certain vivacity and a certain level of luminance) that is non-uniform and that changes as a function of the conditions of observation (light, temperature, angles of observation, etc.). They thereby differ from coloured pigments, which afford a standard uniform opaque, semi-transparent or transparent shade.

Several types of pigments with special effects exist: those with a low refractive index, such as fluorescent or photochromic pigments, and those with a higher refractive index, such as nacres, interference pigments or glitter flakes.

Examples of pigments with special effects that may be mentioned include nacreous pigments such as mica covered with titanium or with bismuth oxychloride, coloured nacreous pigments such as mica covered with titanium and with iron oxides, mica covered with iron oxide, mica covered with titanium and notably with ferric blue or with chromium oxide, mica covered with titanium and with an organic pigment as defined previously, and also nacreous pigments based on bismuth oxychloride.

Nacreous pigments that may be mentioned include the nacres Cellini sold by BASF (mica-$TiO_2$-lake), Prestige sold by Eckart (mica-$TiO_2$), Prestige Bronze sold by Eckart (mica-$Fe_2O_3$) and Colorona sold by Merck (mica-$TiO_2$—$Fe_2O_3$).

Mention may also be made of the gold-coloured nacres sold notably by the company BASF under the name Brilliant gold 212G (Timica), Gold 222C (Cloisonne), Sparkle gold (Timica), Gold 4504 (Chromalite) and Monarch gold 233X (Cloisonne); the bronze nacres sold notably by the company Merck under the name Bronze fine (17384) (Colorona) and Bronze (17353) (Colorona) and by the company BASF under the name Super bronze (Cloisonne); the orange nacres sold notably by the company BASF under the name Orange 363C (Cloisonne) and Orange MCR 101 (Cosmica) and by the company Merck under the name Passion orange (Colorona) and Matte orange (17449) (Microna); the brown nacres sold notably by the company BASF under the name Nu-antique copper 340XB (Cloisonne) and Brown CL4509 (Chromalite); the nacres with a copper tint sold notably by the company BASF under the name Copper 340A (Timica); the nacres with a red tint sold notably by the company Merck under the name Sienna fine (17386) (Colorona); the nacres with a yellow tint sold notably by the company BASF under the name Yellow (4502) (Chromalite); the red nacres with a gold tint sold notably by the company BASF under the name Sunstone G012 (Gemtone); the pink nacres sold notably by the company BASF under the name Tan opale G005 (Gemtone); the black nacres with a gold tint sold notably by the company BASF under the name Nu antique bronze 240 AB (Timica), the blue nacres sold notably by the company Merck under the name Matte blue (17433) (Microna), the white nacres with a silvery tint sold notably by the company Merck under the name Xirona Silver, and the golden-green pink-orange nacres sold notably by the company Merck under the name Indian summer (Xirona), and mixtures thereof.

Still as examples of nacreous agents, mention may also be made of particles including a borosilicate substrate coated with titanium oxide.

Particles comprising a glass substrate coated with titanium oxide are notably sold under the name Metashine MC1080RY by the company Toyal.

Finally, examples of nacres that may also be mentioned include polyethylene terephthalate glitter flakes, notably those sold by the company Meadowbrook Inventions under the name Silver 1P 0.004×0.004 (silver glitter flakes). It is also possible to envisage multilayer pigments based on synthetic substrates, such as alumina, silica, calcium sodium borosilicate, calcium aluminium borosilicate and aluminium.

The pigments with special effects may also be chosen from reflective particles, i.e. notably from particles whose size, structure, notably the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, highlight points that are visible to the naked eye, i.e. brighter points that contrast with their environment, making them appear to sparkle.

The reflective particles may be selected so as not to significantly alter the colouring effect generated by the colouring agents with which they are combined, and more particularly so as to optimize this effect in terms of colour rendition. They may more particularly have a yellow, pink, red, bronze, orange, brown, gold and/or coppery colour or tint.

These particles may have varied forms and may notably be in platelet or globular form, in particular in spherical form.

The reflective particles, whatever their form, may or may not have a multilayer structure and, in the case of a multilayer structure, may have, for example, at least one layer of uniform thickness, notably of a reflective material.

When the reflective particles do not have a multilayer structure, they may be composed, for example, of metal oxides, notably titanium or iron oxides obtained synthetically.

When the reflective particles have a multilayer structure, they may include, for example, a natural or synthetic substrate, notably a synthetic substrate at least partially coated with at least one layer of a reflective material, notably of at least one metal or metallic material. The substrate may be made of one or more organic and/or mineral materials.

More particularly, it may be chosen from glasses, ceramics, graphite, metal oxides, aluminas, silicas, silicates, notably aluminosilicates and borosilicates, and synthetic mica, and mixtures thereof, this list not being limiting.

The reflective material may include a layer of metal or of a metallic material.

Reflective particles are notably described in documents JP-A-09188830, JP-A-10158450, JP-A-10158541, JP-A-07258460 and JP-A-05017710.

Again as an example of reflective particles including a mineral substrate coated with a layer of metal, mention may also be made of particles including a silver-coated borosilicate substrate.

Particles with a silver-coated glass substrate, in the form of platelets, are sold under the name Microglass Metashine REFSX 2025 PS by the company Toyal.

Particles with a glass substrate coated with nickel/chromium/molybdenum alloy are sold under the names Crystal Star GF 550 and GF 2525 by this same company.

Use may also be made of particles comprising a metal substrate, such as silver, aluminium, iron, chromium, nickel, molybdenum, gold, copper, zinc, tin, magnesium, steel, bronze or titanium, said substrate being coated with at least one layer of at least one metal oxide, such as titanium oxide, aluminium oxide, iron oxide, cerium oxide, chromium oxide, silicon oxides and mixtures thereof.

Examples that may be mentioned include aluminium powder, bronze powder or copper powder coated with $SiO_2$ sold under the name Visionaire by the company Eckart.

Mention may also be made of pigments with an interference effect which are not attached to a substrate, such as liquid crystals (Helicones HC from Wacker) or interference holographic glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

The variety of pigments that may be used in the present invention makes it possible to obtain a wide range of colours, and also particular optical effects such as metallic effects or interference effects.

The size of the pigment used in the compositions according to the present invention is generally between 10 nm and 200 μm, preferably between 20 nm and 80 μm and more preferentially between 30 nm and 50 μm.

The pigments may be dispersed in the composition by means of a dispersant.

The dispersant serves to protect the dispersed particles against their agglomeration or flocculation. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. In particular, esters of 12-hydroxystearic acid in particular and of C8 to C20 fatty acid and of polyols such as glycerol or diglycerol are used, such as poly(12-hydroxystearic acid) stearate with a molecular weight of approximately 750 g/mol, such as the product sold under the name Solsperse 21 000 by Avecia, polyglyceryl-2 dipolyhydroxystearate (CTFA name) sold under the reference Dehymyls PGPH by Henkel, or else polyhydroxystearic acid such as the product sold under the reference Arlacel P100 by Unigema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the compositions may be surface-treated with an organic agent.

Thus, the pigments surface-treated beforehand that are useful in the context of the invention are pigments which have been completely or partially subjected to a surface treatment of chemical, electronic, electrochemical, mechanochemical or mechanical nature with an organic agent, such as those described notably in *Cosmetics and Toiletries*, February 1990, Vol. 105, pages 53-64, before being dispersed in the composition in accordance with the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides; polyethylene; (meth)acrylic polymers, for example polymethyl methacrylates; polymers and copolymers containing acrylate units; alkanolamines; silicone compounds, for example silicones, notably polydimethylsiloxanes; organofluorine compounds, for example perfluoroalkyl ethers; fluorosilicone compounds.

The surface-treated pigments that are useful in the composition may also have been treated with a mixture of these compounds and/or may have undergone several surface treatments.

The surface-treated pigments that are useful in the context of the present invention may be prepared according to surface-treatment techniques that are well known to those skilled in the art, or may be commercially available as is.

Preferably, the surface-treated pigments are coated with an organic layer.

The organic agent with which the pigments are treated may be deposited on the pigments by evaporation of solvent, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is notably described in U.S. Pat. No. 4,578,266.

An organic agent covalently bonded to the pigments will preferably be used.

The agent for the surface treatment may represent from 0.1% to 50% by weight of the total weight of the surface-treated pigment, preferably from 0.5% to 30% by weight and even more preferentially from 1% to 20% by weight of the total weight of the surface-treated pigment.

Preferably, the surface treatments of the pigments are chosen from the following treatments:

a PEG-silicone treatment, for instance the AQ surface treatment sold by LCW;

a methicone treatment, for instance the SI surface treatment sold by LCW;

a dimethicone treatment, for instance the Covasil 3.05 surface treatment sold by LCW;

a dimethicone/trimethyl siloxysilicate treatment, for instance the Covasil 4.05 surface treatment sold by LCW;

a magnesium myristate treatment, for instance the MM surface treatment sold by LCW;

an aluminium dimyristate treatment, such as the MI surface treatment sold by Miyoshi;

a perfluoropolymethyl isopropyl ether treatment, for instance the FHC surface treatment sold by LCW;

an isostearyl sebacate treatment, for instance the HS surface treatment sold by Miyoshi;

a perfluoroalkyl phosphate treatment, for instance the PF surface treatment sold by Daito;

an acrylate/dimethicone copolymer and perfluoroalkyl phosphate treatment, for instance the FSA surface treatment sold by Daito;

a polymethylhydrogenosiloxane/perfluoroalkyl phosphate treatment, for instance the FS01 surface treatment sold by Daito;

an acrylate/dimethicone copolymer treatment, for instance the ASC surface treatment sold by Daito;

an isopropyl titanium triisostearate treatment, for instance the ITT surface treatment sold by Daito;

an acrylate copolymer treatment, for instance the APD surface treatment sold by Daito;

a perfluoroalkyl phosphate/isopropyl titanium triisostearate treatment, for instance the PF+ITT surface treatment sold by Daito.

According to a particular embodiment of the invention, the dispersant is present with organic or mineral pigments in submicron-sized particulate form.

The term "submicron" or "submicronic" refers to pigments having a particle size that has been micronized by a micronization method and having a mean particle size of less than a micrometre (μm), in particular between 0.1 and 0.9 μm, and preferably between 0.2 and 0.6 μm.

According to one embodiment, the dispersant and the pigment(s) are present in an amount (dispersant:pigment), according to a weight ratio, of between 1:4 and 4:1, particularly between 1.5:3.5 and 3.5:1 or better still between 1.75:3 and 3:1.

The dispersant(s) may therefore have a silicone backbone, such as silicone polyether and dispersants of amino silicone type. Among the suitable dispersants that may be mentioned are:

aminosilicones, i.e. silicones comprising one or more amino groups such as those sold under the names and references: BYK LPX 21879 by BYK, GP-4, GP-6, GP-344, GP-851, GP-965, GP-967 and GP-988-1, sold by Genesee Polymers, silicone acrylates such as Tego® RC 902, Tego® RC 922, Tego® RC 1041, and Tego® RC 1043, sold by Evonik, polydimethylsiloxane (PDMS) silicones bearing carboxyl groups such as X-22162 and X-22370 by Shin-Etsu, epoxy silicones such as GP-29, GP-32, GP-502, GP-504, GP-514, GP-607, GP-682, and GP-695 by Genesee Polymers, or Tego® RC 1401, Tego® RC 1403, Tego® RC 1412 by Evonik.

According to one specific embodiment, the dispersant(s) are of amino silicone type and are cationic.

Preferably, the pigment(s) are chosen from mineral, mixed mineral-organic or organic pigments.

In one variant of the invention, the pigment(s) are organic pigments, preferentially organic pigments surface-treated with an organic agent chosen from silicone compounds. In another variant of the invention, the pigment(s) are mineral pigments.

Direct Dye

Composition A and/or composition B used in the context of the process according to the invention may comprise one or more direct dyes. In particular, composition B may comprise one or more direct dyes.

The term "direct dye" means natural and/or synthetic dyes, other than oxidation dyes. These are dyes that will spread superficially on the fibre.

They may be ionic or nonionic, preferably cationic or nonionic.

Examples of suitable direct dyes that may be mentioned include azo direct dyes; (poly)methine dyes such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures.

The direct dyes are preferably cationic direct dyes. Mention may be made of the hydrazono cationic dyes of formulae (XIII) and (XIV) and the azo cationic dyes (XV) and (XVI) below:

$$Het^{+}\text{-}N(Ra)—N{=}C(Rb)Ar,Q^{-} \quad (XIII),$$

$$Het^{+}\text{-}C(Ra){=}N—N(Rb)Ar,Q \quad (XIV),$$

$$Het^{+}\text{-}N{=}N—Ar,Q^{-} \quad (XV),$$

$$Ar^{+}—N{=}N—Ar'',Q^{-} \quad (XVI),$$

in which formulae (XIII) to (XVI):

Het+ represents a cationic heteroaryl radical, preferentially bearing an endocyclic cationic charge, such as imidazolium, indolium or pyridinium, which is optionally substituted, preferentially with at least one ($C_1$-$C_8$) alkyl group such as methyl;

Ar+ represents an aryl radical, such as phenyl or naphthyl, bearing an exocyclic cationic charge, preferentially ammonium, particularly tri($C_1$-$C_8$)alkylammonium, such as trimethylammonium;

Ar represents an aryl group, notably phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar" represents an optionally substituted (hetero)aryl group, such as phenyl or pyrazolyl, which are optionally substituted, preferentially with one or more ($C_1$-$C_8$)alkyl, hydroxyl, (di)($C_1$-$C_8$)(alkyl)amino, ($C_1$-$C_8$) alkoxy or phenyl groups;

Ra and Rb, which may be identical or different, represent a hydrogen atom or a ($C_1$-$C_8$)alkyl group, which is optionally substituted, preferentially with a hydroxyl group;

or else the substituent Ra with a substituent of $Het^{+}$ and/or Rb with a substituent of Ar form, together with the atoms that bear them, a (hetero)cycloalkyl; in particular, Ra and Rb represent a hydrogen atom or a ($C_1$-$C_4$) alkyl group optionally substituted with a hydroxyl group;

Q− represents an organic or mineral anionic counterion, such as a halide or an alkyl sulfate.

In particular, mention may be made of the azo and hydrazono direct dyes bearing an endocyclic cationic charge of formulae (XIII) to (XVI) as defined previously, more particularly, the cationic direct dyes bearing an endocyclic cationic charge described in patent applications WO 95/15144, WO 95/01772 and EP 714 954, preferentially the following direct dyes:

(XVII)

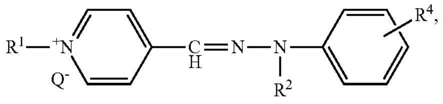

(XVIII)

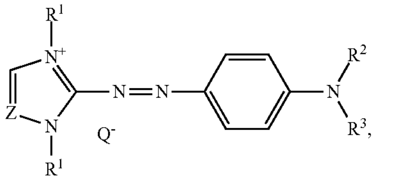

in which formulae (XVII) and (XVIII):

$R^1$ represents a $(C_1-C_4)$alkyl group such as methyl;

$R^2$ and $R^3$, which may be identical or different, represent a hydrogen atom or a $(C_1-C_4)$alkyl group, such as methyl; and $R^4$ represents a hydrogen atom or an electron-donating group such as optionally substituted $(C_1-C_8)$alkyl, optionally substituted $(C_1-C_8)$alkoxy, or (di)$(C_1-C_8)$(alkyl)amino optionally substituted on the alkyl group (s) with a hydroxyl group; in particular, $R^4$ is a hydrogen atom;

Z represents a CH group or a nitrogen atom, preferentially CH,

Q− is an anionic counterion as defined previously, in particular a halide, such as chloride, or an alkyl sulfate, such as methyl sulfate or mesyl.

In particular, the dyes of formulae (XV) and (XVI) are chosen from Basic Red 51, Basic Yellow 87 and Basic Orange 31 or derivatives thereof with Q' being an anionic counterion as defined previously, particularly a halide such as chloride, or an alkyl sulfate such as methyl sulfate or mesyl.

The direct dyes may be chosen from anionic direct dyes. The anionic direct dyes of the invention are dyes commonly referred to as "acid" direct dyes owing to their affinity for alkaline substances. The term "anionic direct dye" means any direct dye including in its structure at least one $CO_2R$ or $SO_3R$ substituent with R denoting a hydrogen atom or a cation originating from a metal or an amine, or an ammonium ion. The anionic dyes may be chosen from direct nitro acid dyes, azo acid dyes, azine acid dyes, triarylmethane acid dyes, indoamine acid dyes, anthraquinone acid dyes, indigoid dyes and natural acid dyes.

As acid dyes that are useful for the invention, mention may be made of the dyes of formulae (XIX), (XIX'), (XX), (XX'), (XXI), (XXI'), (XXII), (XXII'), (XXIII), (XXIV), (XXV) and (XXVI) below:

a) the diaryl anionic azo dyes of formula (XIX) or (XIX'):

(XIX)

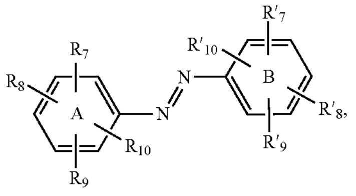

-continued (XIX')

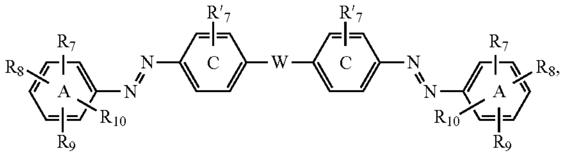

in which formulae (XIX) and (XIX'):

$R_7$, $R_8$, $R_9$, $R_{10}$, $R'_7$, $R'_8$, $R'_9$ and $R'_{10}$, which may be identical or different, represent a hydrogen atom or a group chosen from:

alkyl;

alkoxy, alkylthio;

hydroxyl, mercapto;

nitro, nitroso;

R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom, or NR with R representing a hydrogen atom or an alkyl group;

$(O)_2S(O^-)$—, $M^+$ with $M^+$ representing a hydrogen atom or a cationic counterion;

$(O)CO^-$—, $M^+$ with $M^+$ as defined previously;

R"—$S(O)_2$—, with R" representing a hydrogen atom or an alkyl, aryl, (di)(alkyl)amino or aryl(alkyl)amino group; preferentially a phenylamino or phenyl group;

R'"—$S(O)_2$—X'— with R'" representing an optionally substituted alkyl or aryl group, X' as defined previously;

(di)(alkyl)amino;

aryl(alkyl)amino optionally substituted with one or more groups chosen from i) nitro; ii) nitroso; iii) $(O)_2S(O^-)$—, $M^+$ and iv) alkoxy with $M^+$ as defined previously;

optionally substituted heteroaryl; preferentially a benzothiazolyl group;

cycloalkyl, notably cyclohexyl;

Ar—N=N— with Ar representing an optionally substituted aryl group; preferentially a phenyl optionally substituted with one or more alkyl, $(O)_2S(O^-)$—, $M^+$ or phenylamino groups;

or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) R°—C(X)—X'—; viii) R°—X'—C(X)—; ix) R°—X'—C(X)—X"—; x) Ar—N=N— and xi) optionally substituted aryl(alkyl)amino; with $M^+$, R°, X, X', X" and Ar as defined previously;

W represents a sigma bond σ, an oxygen or sulfur atom, or a divalent radical i) —NR— with R as defined previously, or ii) methylene —C(Ra)(Rb)- with Ra and Rb, which may be identical or different, representing a hydrogen atom or an aryl group, or alternatively Ra and Rb form, together with the carbon atom that bears them, a spiro cycloalkyl; preferentially, W represents a sulfur atom or Ra and Rb together form a cyclohexyl;

it being understood that formulae (XIX) and (XIX') comprise at least one sulfonate radical $(O)_2S(O^-)$—, $M^+$ or one carboxylate radical $(O)CO^-$—, $M^+$ on one of the rings A, A', B, B' or C; preferentially sodium sulfonate.

As examples of dyes of formula (XIX), mention may be made of: Acid Red 1, Acid Red 4, Acid Red 13, Acid Red 14, Acid Red 18, Acid Red 27, Acid Red 28, Acid Red 32, Acid Red 33, Acid Red 35, Acid Red 37, Acid Red 40, Acid Red 41, Acid Red 42, Acid Red 44, Pigment Red 57, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Yellow 6, Acid Yellow 9, Acid Yellow 36, Acid Yellow 199, Food Yellow 3, Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Food Yellow 3 or Sunset Yellow;

and, as examples of dyes of formula (XIX'), mention may be made of: Acid Red 111, Acid Red 134, Acid Yellow 38;

b) the pyrazolone anionic azo dyes of formulae (XX) and (XX'):

Ar—O—$S(O)_2$— with Ar representing an optionally substituted aryl group; preferentially a phenyl optionally substituted with one or more alkyl groups;

$R_{19}$ and $R_{20}$ together form either a double bond, or a benzo group D', which is optionally substituted;

$R'_{16}$, $R'_{19}$ and $R'_{20}$, which may be identical or different, represent a hydrogen atom or an alkyl or hydroxyl group;

$R_{21}$ represents a hydrogen atom or an alkyl or alkoxy group;

Ra and Rb, which may be identical or different, are as defined previously; preferentially, Ra represents a hydrogen atom and Rb represents an aryl group;

Y represents either a hydroxyl group or an oxo group;

---- represents a single bond when Y is an oxo group; and represents a double bond when Y represents a hydroxyl group;

it being understood that formulae (XX) and (X') comprise at least one sulfonate radical $(O)_2S(O^-)$—, $M^+$ or one carboxylate radical —C(O)O—, $M^+$ on one of the rings D or E; preferentially sodium sulfonate.

As examples of dyes of formula (XX), mention may be made of: Acid Red 195, Acid Yellow 23, Acid Yellow 27, (XX)

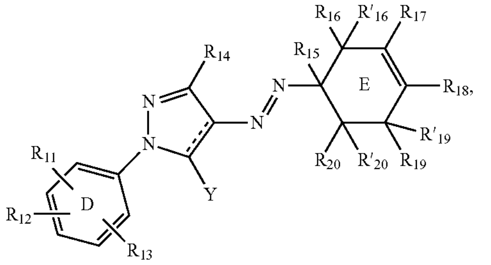

(XX')

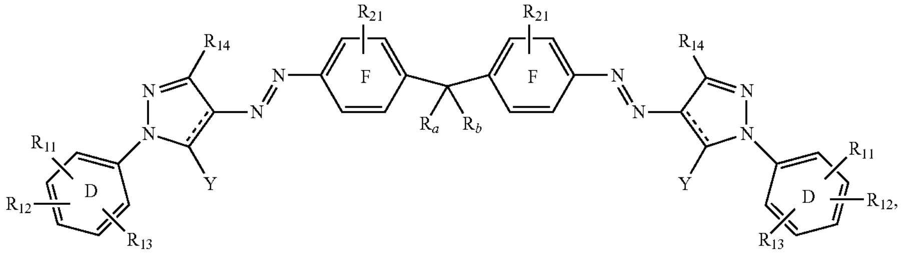

Acid Yellow 76, and as examples of dyes of formula (XX'), mention may be made of: Acid Yellow 17;

in which formulae (XX) and (XX'):

$R_{11}$, $R_{12}$ and $R_{13}$, which may be identical or different, represent a hydrogen or halogen atom, an alkyl group or —$(O)_2S(O^-)$, $M^+$ with $M^+$ as defined previously;

$R_{14}$ represents a hydrogen atom, an alkyl group or a group —C(O)O, $M^+$ with $M^+$ as defined previously;

$R_{15}$ represents a hydrogen atom;

$R_{16}$ represents an oxo group, in which case $R'_{16}$ is absent, or alternatively $R_{15}$ with $R_{16}$ together form a double bond;

$R_{17}$ and $R_{18}$, which may be identical or different, represent a hydrogen atom, or a group chosen from:

$(O)_2S(O^-)$—, $M^+$ with $M^+$ as defined previously;

c) the anthraquinone dyes of formulae (XXI) and (XXI'):

(XXI)

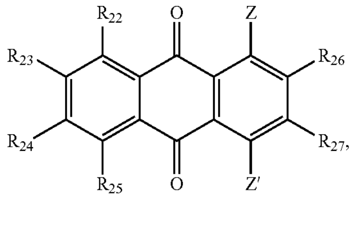

-continued (XXI')

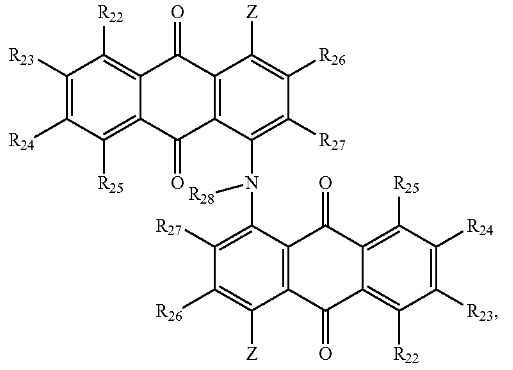

in which formulae (XXI) and (XXI'):

- $R_{22}$, $R_{23}$, $R_{24}$, $R_{25}$, $R_{26}$ and $R_{27}$, which may be identical or different, represent a hydrogen or halogen atom, or a group chosen from:
- alkyl;
- hydroxyl, mercapto;
- alkoxy, alkylthio;
- optionally substituted aryloxy or arylthio, preferentially substituted with one or more groups chosen from alkyl and $(O)_2S(O^-)$—, $M^+$ with $M^+$ as defined previously;
- aryl(alkyl)amino optionally substituted with one or more groups chosen from alkyl and $(O)_2S(O^-)$—, $M^+$ with $M^+$ as defined previously;
- (di)(alkyl)amino;
- (di)(hydroxyalkyl)amino;
- $(O)_2S(O^-)$—, $M^+$ with $M^+$ as defined previously;
- Z' represents a hydrogen atom or a group $NR_{28}R_{29}$ with $R_{28}$ and $R_{29}$, which may be identical or different, representing a hydrogen atom or a group chosen from:
- alkyl;
- polyhydroxyalkyl such as hydroxyethyl;
- aryl optionally substituted with one or more groups, particularly i) alkyl such as methyl, n-dodecyl, n-butyl; ii) $(O)_2S(O^-)$—, $M^+$ with $M^+$ as defined previously; iii) R°—C(X)—X'—, R°—X'—C(X)—, R°—X'—C(X)—X"— with R°, X, X' and X" as defined previously, preferentially R° represents an alkyl group;
- cycloalkyl; notably cyclohexyl;
- Z represents a group chosen from hydroxyl and $NR'_{28}R'_{29}$ with $R'_{28}$ and $R'_{29}$, which may be identical or different, representing the same atoms or groups as $R_{28}$ and $R_{29}$ as defined previously;

it being understood that formulae (XXI) and (XXI') comprise at least one sulfonate radical $(O)_2S(O^-)$—, $M^+$ or one carboxylate radical C(O)O—, $M^+$; preferentially sodium sulfonate.

As examples of dyes of formula (XXI), mention may be made of: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3; EXT Violet No. 2; and, as an example of a dye of formula (XXI'), mention may be made of: Acid Black 48.

d) the nitro dyes of formulae (XXII) and (XXII'):

(XXII)

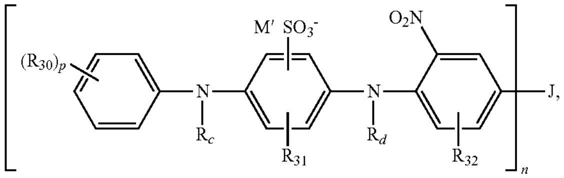

(XXII')

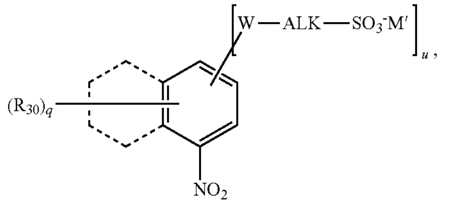

in which formulae (XII) and (XII'):

- $R_{30}$, $R_{31}$ and $R_{32}$, which may be identical or different, represent a hydrogen or halogen atom, or a group chosen from:
- alkyl;
- alkoxy optionally substituted with one or more hydroxyl groups, alkylthio optionally substituted with one or more hydroxyl groups;
- hydroxyl, mercapto;
- nitro, nitroso;
- polyhaloalkyl;
- R°—C(X)—X'—, R°—X'—C(X)—, R°—X'—C(X)—X"— with R°, X, X' and X" as defined previously;
- $(O)_2S(O^-)$—, $M^+$ with $M^+$ as defined previously;
- $(O)CO^-$—, $M^+$ with $M^+$ as defined previously;
- (di)(alkyl)amino;
- (di)(hydroxyalkyl)amino;
- heterocycloalkyl such as piperidino, piperazino or morpholino; in particular, $R_{30}$, $R_{31}$ and $R_{32}$ represent a hydrogen atom;
- Rc and Rd, which may be identical or different, represent a hydrogen atom or an alkyl group;
- W is as defined previously; W particularly represents an —NH— group;
- ALK represents a linear or branched divalent $C_1$-$C_6$ alkylene group; in particular, ALK represents a $—CH_2—CH_2—$ group;
- n is 1 or 2;
- p represents an integer inclusively between 1 and 5;
- q represents an integer inclusively between 1 and 4;
- u is 0 or 1;
- when n is 1, J represents a nitro or nitroso group; particularly nitro;
- when n is 2, J represents an oxygen or sulfur atom, or a divalent radical $—S(O)_m—$ with m representing an integer 1 or 2; preferentially, J represents an $—SO_2$-radical;
- M' represents a hydrogen atom or a cationic counterion;

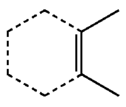
, which may be present or absent, represents a benzo group optionally substituted with one or more groups $R_{30}$ as defined previously;

it being understood that formulae (XXII) and (XXII') comprise at least one sulfonate radical $(O)_2S(O^-)$—, $M^+$ or one carboxylate radical C(O)O, $M^+$; preferentially sodium sulfonate.

As examples of dyes of formula (XXII), mention may be made of: Acid Brown 13 and Acid Orange 3; as examples of dyes of formula (XXII'), mention may be made of: Acid Yellow 1, the sodium salt of 2,4-dinitro-1-naphthol-7-sulfonic acid, 2-piperidino-5-nitrobenzenesulfonic acid, 2-(4'-N, N-(2"-hydroxyethyl)amino-2'-nitro)anilineethanesulfonic acid, 4-O-hydroxyethylamino-3-nitrobenzenesulfonic acid; EXT D&C Yellow 7;

e) the triarylmethane dyes of formula (XXIII):

(XXIII)

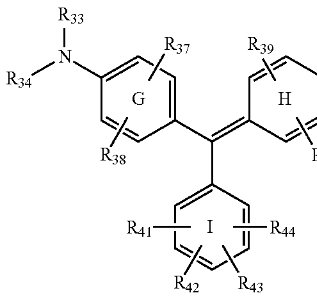

in which formula (XXIII):

$R_{33}$, $R_{34}$, $R_{35}$ and $R_{36}$, which may be identical or different, represent a hydrogen atom or a group chosen from alkyl, optionally substituted aryl and optionally substituted arylalkyl; particularly an alkyl and benzyl group optionally substituted with a group $(O)_mS(O^-)$—, $M^+$ with $M^+$ and m as defined previously;

$R_{37}$, $R_{38}$, $R_{39}$, $R_{40}$, $R_{41}$, $R_{42}$, $R_{43}$ and $R_{44}$, which may be identical or different, represent a hydrogen atom or a group chosen from:

alkyl;

alkoxy, alkylthio;

(di)(alkyl)amino;

hydroxyl, mercapto;

nitro, nitroso;

R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom, or NR with R representing a hydrogen atom or an alkyl group;

$(O)_2S(O^-)$—, $M^+$ with $M^+$ representing a hydrogen atom or a cationic counterion;

$(O)CO^-$—, $M^+$ with $M^+$ as defined previously;

or alternatively two contiguous groups $R_{41}$ with $R_{42}$ or $R_{42}$ with $R_{43}$ or $R_{43}$ with $R_{44}$ together form a fused benzo group: I'; with I' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) R°—C(X)—X'—; viii) R°—X'—C(X)— and ix) R°—X'—C(X)—X"—; with $M^+$, R°, X, X' and X" as defined previously;

in particular, $R_{37}$ to $R_{40}$ represent a hydrogen atom, and $R_{41}$ to $R_{44}$, which may be identical or different, represent a hydroxyl group or $(O)_2S(O^-)$—, $M^+$; and when $R_{43}$ with $R_{44}$ together form a benzo group, it is preferentially substituted with an $(O)_2S(O^-)$— group;

it being understood that at least one of the rings G, H, I or I' comprises at least one sulfonate radical $(O)_2S(O^-)$— or one carboxylate radical —C(O)O—; preferentially sulfonate.

As examples of dyes of formula (XXIII), mention may be made of: Acid Blue 1; Acid Blue 3; Acid Blue 7, Acid Blue 9; Acid Violet 49; Acid Green 3; Acid Green 5 and Acid Green 50.

f) the xanthene-based dyes of formula (XXIV):

(XXIV)

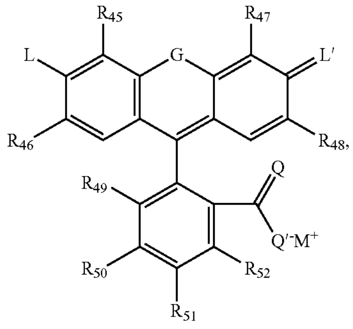

in which formula (XXIV):

$R_{45}$, $R_{46}$, $R_{47}$ and $R_{48}$, which may be identical or different, represent a hydrogen or halogen atom;

$R_{49}$, $R_{50}$, $R_{51}$ and $R_{52}$, which may be identical or different, represent a hydrogen or halogen atom, or a group chosen from:

alkyl;

alkoxy, alkylthio;

hydroxyl, mercapto;

nitro, nitroso;

$(O)_2S(O^-)$—, $M^+$ with $M^+$ representing a hydrogen atom or a cationic counterion;

$(O)CO^-$—, $M^+$ with $M^+$ as defined previously;

particularly, $R_{49}$, $R_{50}$, $R_{51}$ and $R_{52}$ represent a hydrogen or halogen atom;

G represents an oxygen or sulfur atom or a group NRe with Re as defined previously; particularly, G represents an oxygen atom;

L represents an alkoxide $O^-$, $M^+$; a thioalkoxide $S^-$, $M^+$ or a group NRf, with Rf representing a hydrogen atom or an alkyl group, and $M^+$ as defined previously; $M^+$ is particularly sodium or potassium;

L' represents an oxygen or sulfur atom or an ammonium group: $N^+$RfRg, with Rf and Rg, which may be identical or different, representing a hydrogen atom or an optionally substituted alkyl or aryl group; L' particularly represents an oxygen atom or a phenylamino group optionally substituted with one or more alkyl or $(O)_mS(O^-)$—, $M^+$ groups with m and $M^+$ as defined previously;

Q and Q', which may be identical or different, represent an oxygen or sulfur atom; particularly, Q and Q' represent an oxygen atom;

$M^+$ is as defined previously.

As examples of dyes of formula (XXIV), mention may be made of: Acid Yellow 73; Acid Red 51; Acid Red 52; Acid Red 87; Acid Red 92; Acid Red 95; Acid Violet 9.

g) the indole-based dyes of formula (XXV):

(XXV)

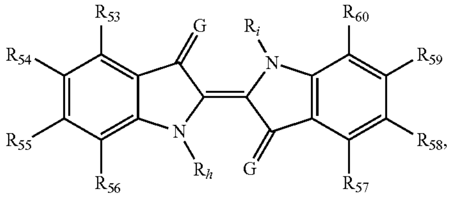

in which formula (XXV):

$R_{53}$, $R_{54}$, $R_{55}$, $R_{56}$, $R_{57}$, $R_{58}$, $R_{59}$ and $R_{60}$, which may be identical or different, represent a hydrogen atom or a group chosen from:

alkyl;

alkoxy, alkylthio;

hydroxyl, mercapto;

nitro, nitroso;

R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom, or NR with R representing a hydrogen atom or an alkyl group;

$(O)_2S(O^-)$—, $M^+$ with $M^+$ representing a hydrogen atom or a cationic counterion;

$(O)CO^-$—, $M^+$ with $M^+$ as defined previously;

G represents an oxygen or sulfur atom or a group NRe with Re as defined previously; particularly, G represents an oxygen atom;

Ri and Rh, which may be identical or different, represent a hydrogen atom or an alkyl group;

it being understood that formula (XXV) comprises at least one sulfonate radical $(O)_2S(O^-)$—, $M^+$ or one carboxylate radical —C(O)O—, $M^+$; preferentially sodium sulfonate.

As examples of dyes of formula (XXV), mention may be made of: Acid Blue 74;

h) the quinoline-based dyes of formula (XXVI):

(XXVI)

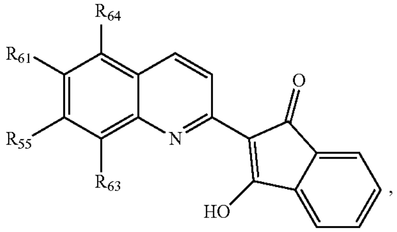

in which formula (XXVI):

$R_{61}$ represents a hydrogen or halogen atom or an alkyl group;

$R_{62}$, $R_{63}$ and $R_{64}$, which may be identical or different, represent a hydrogen atom or a group $(O)_2S(O^-)$—, $M^+$ with $M^+$ representing a hydrogen atom or a cationic counterion;

or alternatively $R_{61}$ with $R_{62}$, or $R_{61}$ with $R_{64}$, together form a benzo group optionally substituted with one or more groups $(O)_2S(O^-)$—, $M^+$ with $M^+$ representing a hydrogen atom or a cationic counterion;

it being understood that formula (XXVI) comprises at least one sulfonate radical $(O)_2S(O^-)$—, $M^+$, preferentially sodium sulfonate.

As examples of dyes of formula (XXVI), mention may be made of: Acid Yellow 2, Acid Yellow 3 and Acid Yellow 5.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Use may also be made of extracts or decoctions containing these natural dyes and notably henna-based poultices or extracts.

Preferably, the direct dyes are chosen from anionic direct dyes.

The colouring agent(s) may be present in a total content ranging from 0.001% to 20% by weight and preferably from 0.005% to 15% by weight relative to the total weight of composition A and/or composition B, preferably, the colouring agent(s) are chosen from pigments.

The pigment(s) may be present in a total content ranging from 0.05% to 20% by weight, preferably from 0.1% to 15% by weight and better still from 5% to 15% by weight, relative to the total weight of composition A and/or composition B.

The direct dye(s) may be present in a total content ranging from 0.001% to 10% by weight of the total weight of the composition, preferably from 0.005% to 5% by weight of the total weight of composition A and/or composition B.

The colouring agent(s) may be present in a total content ranging from 0.001% to 20% by weight and preferably from 0.005% to 15% by weight relative to the total weight of composition C.

The pigment(s) may be present in a total content ranging from 0.05% to 20% by weight, preferably from 0.1% to 15% by weight and better still from 0.5% to 10% by weight, relative to the total weight of composition C.

The direct dye(s) may be present in a total content ranging from 0.001% to 10% by weight relative to the total weight of the composition, preferably from 0.005% to 5% by weight relative to the total weight of composition C.

Silicone

One and/or the other of the compositions A and B may also comprise at least one silicone.

The silicone(s) are different from the compound(s) containing at least one carboxylic acid group.

Preferably, one and/or the other of the compositions A and B comprises at least one silicone chosen from non-amino silicones, amino silicones and mixtures thereof.

The silicones may be solid or liquid at 25° C. and atmospheric pressure ($1.013\times10^5$ Pa), and volatile or non-volatile.

The silicones that may be used may be soluble or insoluble in the composition according to the invention; they may be in the form of oil, wax, resin or gum; silicone oils are preferred.

Silicones are in particular described in detail in Walter Noll's *Chemistry and Technology of Silicones* (1968), Academic Press.

Preferably, one and/or the other of the compositions A and B contains one or more silicones that are liquid at 25° C. and atmospheric pressure ($1.013\times10^5$ Pa).

The volatile silicones may be chosen from those with a boiling point of between 60° C. and 260° C. (at atmospheric pressure) and more particularly from:

i) cyclic polydialkylsiloxanes including from 3 to 7 and preferably 4 to 5 silicon atoms, such as octamethylcyclotetrasiloxane and decamethylcyclopentasiloxane.

Mention may be made of the products sold under the name Volatile Silicone 7207 by Union Carbide or Silbione 70045 V 2 by Rhodia, Volatile Silicone 7158 by Union Carbide or Silbione 70045 V 5 by Rhodia;

cyclocopolymers of the dimethylsiloxane/methylalkylsiloxane type having the chemical structure:

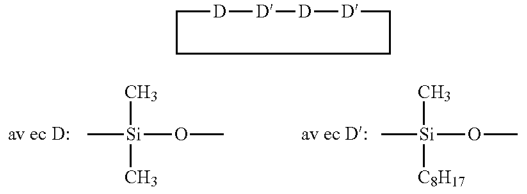

Preferably cyclomethylsiloxane.

Mention may be made of Volatile Silicone FZ 3109 sold by the company Union Carbide.

mixtures of cyclic silicones with silicon-derived organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

ii) linear polydialkylsiloxanes containing 2 to 9 silicon atoms, which generally have a viscosity of less than or equal to $5\times10^{-6}$ $m^2/s$ at 25° C., such as decamethyltetrasiloxane.

Other silicones belonging to this category are described in the article published in Cosmetics and Toiletries, Vol. 91, January 76, pages 27-32—Todd & Byers *Volatile silicone fluids for cosmetics*; mention may be made of the product sold under the name SH 200 by the company Toray Silicone.

Among the non-volatile silicones, mention may be made, alone or as a mixture, of polydialkylsiloxanes and notably polydimethylsiloxanes (PDMS), polydiarylsiloxanes, polyalkylarylsiloxanes, silicone gums and resins, and also organopolysiloxanes (or organomodified polysiloxanes, or alternatively organomodified silicones) which are polysiloxanes including in their structure one or more organofunctional groups, generally attached via a hydrocarbon-based group, and preferably chosen from aryl groups, amine groups, alkoxy groups and polyoxyethylene or polyoxypropylene groups. Preferably, the non-volatile silicones are chosen from polydimethyl/methylsiloxanes which are optionally oxyethylenated and oxypropylenated.

The organomodified silicones may be polydiarylsiloxanes, notably polydiphenylsiloxanes, and polyalkylarylsiloxanes functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of organopolysiloxanes including:

polyoxyethylene and/or polyoxypropylene groups optionally including $C_6$-$C_{24}$ alkyl groups, such as dimethicone copolyols, and notably those sold by the company Dow Corning under the name DC 1248 or the oils Silwet® L 722, L 7500, L 77 and L 711 from the company Union Carbide; or alternatively (C12)alkylmethicone copolyols, and notably those sold by the company Dow Corning under the name Q2-5200;

substituted or unsubstituted amine groups, in particular C1-C4 aminoalkyl groups; mention may be made of the products sold under the name GP4 Silicone Fluid and GP7100 by the company Genesee, or under the names Q2-8220 and DC929 or DC939 by the company Dow Corning;

thiol groups, such as the products sold under the names GP 72 A and GP 71 from Genesee;

alkoxylated groups, such as the product sold under the name Silicone Copolymer F-755 by SWS Silicones and Abil Wax® 2428, 2434 and 2440 by the company Goldschmidt;

hydroxylated groups, for instance polyorganosiloxanes bearing a hydroxyalkyl function;

acyloxyalkyl groups, such as the polyorganosiloxanes described in U.S. Pat. No. 4,957,732;

anionic groups of the carboxylic acid type, as described, for example, in EP 186 507, or of the alkylcarboxylic type, such as the product X-22-3701E from the company Shin-Etsu; or alternatively of the 2-hydroxyalkylsulfonate or 2-hydroxyalkylthiosulfate type, such as the products sold by the company Goldschmidt under the names Abil® S201 and Abil® S255;

hydroxyacylamino groups, such as the polyorganosiloxanes described in patent application EP 342 834; mention may be made, for example, of the product Q2-8413 from the company Dow Corning.

The silicones may also be chosen from polydialkylsiloxanes, among which mention may be made mainly of polydimethylsiloxanes bearing trimethylsilyl end groups. Among these polydialkylsiloxanes, mention may be made of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200, with a viscosity of 60 000 $mm^2/s$;

the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C1-C20)dialkylsiloxanes.

Products that may be used more particularly in accordance with the invention are mixtures such as:

mixtures formed from a polydimethylsiloxane with a hydroxy-terminated chain, or dimethiconol (CTFA), and from a cyclic polydimethylsiloxane, also known as cyclomethicone (CTFA), such as the product Q2-1401 sold by the company Dow Corning, mixtures formed from a polydimethylsiloxane with a hydroxy-terminated chain, or dimethiconol (CTFA), and from a polydimethylsiloxane, also known as dimethicone (CTFA), such as the product Xiameter® PMX-1503 Fluid sold by the company Dow Corning.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ $m^2/s$ at 25° C.

Among these polyalkylarylsiloxanes, mention may be made of the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Preferably, one and/or the other of the compositions A and B comprises at least one amino silicone. The term “amino silicone” denotes any silicone including at least one primary, secondary or tertiary amine or a quaternary ammonium group.

The weight-average molecular masses of these amino silicones may be measured by gel permeation chromatography (GPC) at room temperature (25° C.), as polystyrene equivalent. The columns used are μ styragel columns. The eluent is THE and the flow rate is 1 ml/min. 200 μl of a 0.5% by weight solution of silicone in THE are injected. Detection is performed by refractometry and UV-metry.

Preferably, the amino silicone(s) that may be used in the context of the invention are chosen from:

a) the polysiloxanes corresponding to formula (A):

(A)

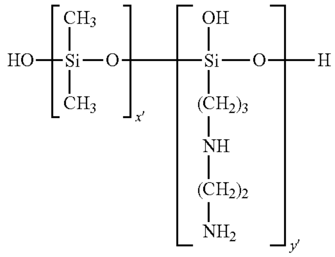

in which x' and y' are integers such that the weight-average molecular weight (Mw) is between 5000 and 500 000 approximately;

b) the amino silicones corresponding to formula (B):

$$R'_aG_{3-a}\text{-}Si(OSiG_2)_n\text{-}(OSiG_bR'_{2-b})_m\text{-}O\text{—}SiG_{3-a}\text{-}R'_a \quad (B)$$

in which:

G, which may be identical or different, denotes a hydrogen atom or a group from among phenyl, OH, $C_1$-$C_8$ alkyl, for example methyl, or $C_1$-$C_8$ alkoxy, for example methoxy;

a, which may be identical or different, denotes 0 or an integer from 1 to 3, in particular 0, b denotes 0 or 1, in particular 1, m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

R', which may be identical or different, denotes a monovalent radical of formula —CqH2qL in which q is a number ranging from 2 to 8 and L is an optionally quaternized amine group chosen from the following groups: —N(R")2; —N+(R")3 A-; —NR"-Q-N(R")2 and —NR"-Q-N+(R")3 A-, in which R", which may be identical or different, denotes hydrogen, phenyl, benzyl, or a saturated monovalent hydrocarbon-based radical, for example a $C_1$-$C_{20}$ alkyl radical; Q denotes a linear or branched group of formula $C_rH_{2r}$, r being an integer ranging from 2 to 6, preferably from 2 to 4; and A– represents a cosmetically acceptable anion, notably a halide anion such as fluoride, chloride, bromide or iodide.

Preferably, the amino silicone(s) are chosen from the amino silicones of formula (B). Preferably, the amino silicones of formula (B) are chosen from the amino silicones corresponding to formulae (C), (D), (E), (F) and/or (G) below.

According to a first embodiment, the amino silicones corresponding to formula (B) are chosen from the silicones known as “trimethylsilyl amodimethicone” corresponding to formula (C):

(C)

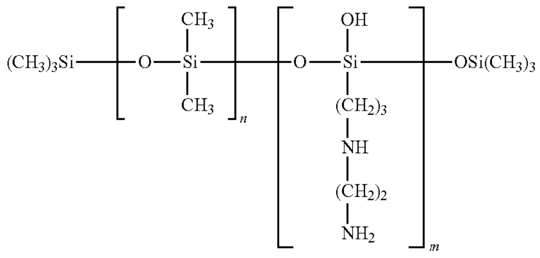

in which m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10.

According to a second embodiment, the amino silicones corresponding to formula (B) are chosen from the silicones of formula (D) below:

(D)

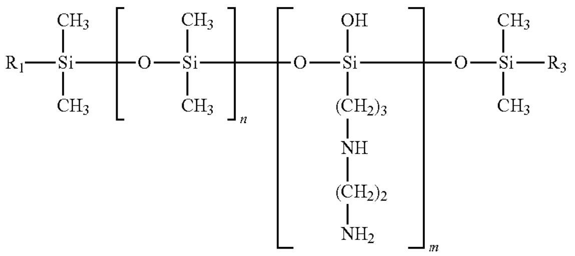

in which:

m and n are numbers such that the sum (n+m) ranges from 1 to 1000, in particular from 50 to 250 and more particularly from 100 to 200; n possibly denoting a number from 0 to 999, notably from 49 to 249 and more particularly from 125 to 175, and m possibly denoting a number from 1 to 1000, notably from 1 to 10 and more particularly from 1 to 5;

$R_1$, $R_2$ and $R_3$, which may be identical or different, represent a hydroxyl or $C_1$-$C_4$ alkoxy radical, at least one of the radicals $R_1$ to $R_3$ denoting an alkoxy radical.

Preferably, the alkoxy radical is a methoxy radical.

The hydroxy/alkoxy mole ratio preferably ranges from 0.2:1 to 0.4:1 and preferably from 0.25:1 to 0.35:1 and more particularly is equal to 0.3:1.

The weight-average molecular mass (Mw) of these silicones preferably ranges from 2000 to 1 000 000 and more particularly from 3500 to 200 000.

According to a third embodiment, the amino silicones corresponding to formula (B) are chosen from the silicones of formula (E) below:

(E)

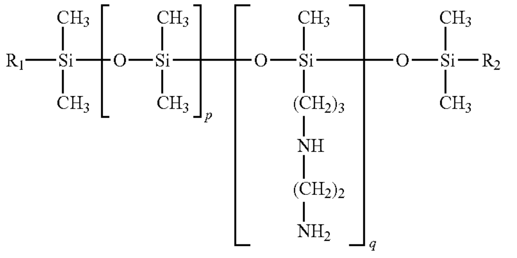

in which:

p and q are numbers such that the sum (p+q) ranges from 1 to 1000, in particular from 50 to 350 and more particularly from 150 to 250; p possibly denoting a number from 0 to 999 and notably from 49 to 349 and more particularly from 159 to 239, and q possibly denoting a number from 1 to 1000, notably from 1 to 10 and more particularly from 1 to 5;

$R_1$ and $R_2$, which are different, represent a hydroxyl or $C_1$-$C_4$ alkoxy radical, at least one of the radicals $R_1$ or $R_2$ denoting an alkoxy radical.

Preferably, the alkoxy radical is a methoxy radical.

The hydroxy/alkoxy mole ratio generally ranges from 1:0.8 to 1:1.1 and preferably from 1:0.9 to 1:1 and more particularly is equal to 1:0.95.

The weight-average molecular mass (Mw) of the silicone preferably ranges from 2000 to 200 000, even more particularly from 5000 to 100 000 and more particularly from 10 000 to 50 000.

The commercial products comprising silicones of structure (D) or (E) may include in their composition one or more other amino silicones the structure of which is different from formula (D) or (E).

A product containing amino silicones of structure (D) is sold by the company Wacker under the name Belsil® ADM 652.

A product containing amino silicones of structure (E) is sold by Wacker under the name Fluid WR 1300® or under the name Belsil® ADM LOG 1.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or non-ionic. The number-average size of the silicone particles in the emulsion generally ranges from 3 nm to 500 nanometers. Preferably, notably as amino silicones of formula (E), use is made of microemulsions with a mean particle size ranging from 5 nm to 60 nm (limits included) and more particularly from 10 nm to 50 nm (limits included). Thus, use may be made according to the invention of the amino silicone microemulsions of formula (E) sold under the names Finish CT 96 E® or SLM 28020® by the company Wacker.

According to a fourth embodiment, the amino silicones corresponding to formula (B) are chosen from the silicones of formula (F) below:

(F)

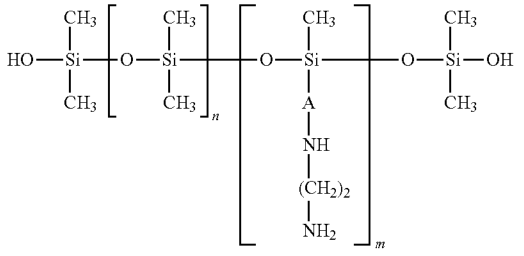

in which:

m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

A denotes a linear or branched alkylene radical containing from 4 to 8 carbon atoms and preferably 4 carbon atoms. This radical is preferably linear.

The weight-average molecular mass (Mw) of these amino silicones preferably ranges from 2000 to 1 000 000 and even more particularly from 3500 to 200 000.

A silicone corresponding to formula (B) is, for example, the Xiameter MEM 8299 Emulsion from Dow Corning (INCI name: amodimethicone and trideceth-6 and cetrimonium chloride).

According to a fifth embodiment, the amino silicones corresponding to formula (B) are chosen from the silicones of formula (G) below:

(G)

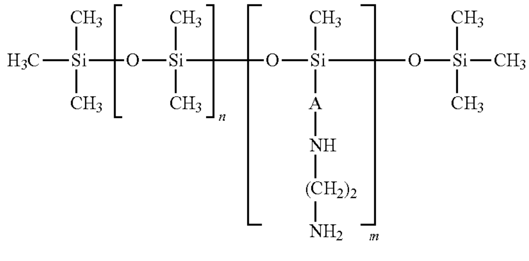

in which:

m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

A denotes a linear or branched alkylene radical containing from 4 to 8 carbon atoms and preferably 4 carbon atoms. This radical is preferably branched.

The weight-average molecular mass (Mw) of these amino silicones preferably ranges from 500 to 1 000 000 and even more particularly from 1000 to 200 000.

A silicone corresponding to this formula is, for example, DC2-8566 Amino Fluid from Dow Corning;

c) the amino silicones corresponding to formula (H):

(H)

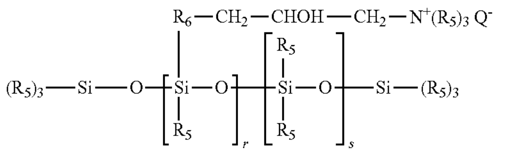

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, notably a $C_1$-$C_{18}$ alkylene radical or a divalent $C_1$-$C_{18}$, for example $C_1$-$C_8$, alkyleneoxy radical linked to the Si via an SiC bond;

$Q^-$ is an anion such as a halide ion, notably chloride, or an organic acid salt, notably acetate;

r represents a mean statistical value ranging from 2 to 20 and in particular from 2 to 8;

s represents a mean statistical value ranging from 20 to 200 and in particular from 20 to 50.

Such amino silicones are notably described in U.S. Pat. No. 4,185,087.

d) the quaternary ammonium silicones of formula (I):

(I)

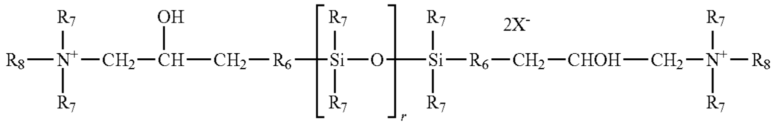

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;

$R_6$ represents a divalent hydrocarbon-based radical, notably a $C_1$-$C_{18}$ alkylene radical or a divalent $C_1$-$C_{18}$, for example $C_1$-$C_8$, alkyleneoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—$NHCOR_7$;

$X^-$ is an anion such as a halide ion, notably chloride, or an organic acid salt, notably acetate;

r represents a mean statistical value ranging from 2 to 200 and in particular from 5 to 100.

These silicones are described, for example, in patent application EP-A 0 530 974;

e) the amino silicones of formula (J):

(J)

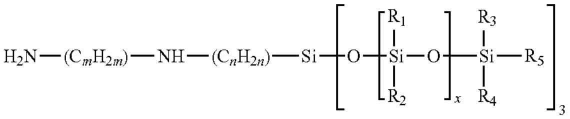

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and x is chosen such that the amine number ranges from 0.01 to 1 meq/g;

f) multiblock polyoxyalkylene amino silicones, of the type $(AB)_n$, A being a polysiloxane block and B being a polyoxyalkylene block including at least one amine group.

Said silicones are preferably formed from repeating units having the following general formulae:

$$[—(SiMe_2O)_xSiMe_2\text{-}R—N(R'')—R'—O(C_2H_4O)_a(C_3H_6O)_b—R'—N(H)—R—]$$

or alternatively $$[—(SiMe_2O)xSiMe_2\text{-}R—N(R'')—R'—O(C_2H_4O)_a(C_3H_6O)_b—]$$

in which:

a is an integer greater than or equal to 1, preferably ranging from 5 to 200 and more particularly ranging from 10 to 100;

b is an integer between 0 and 200, preferably ranging from 4 to 100 and more particularly between 5 and 30;

x is an integer ranging from 1 to 10 000 and more particularly from 10 to 5000;

R" is a hydrogen atom or a methyl;

R, which may be identical or different, represent a linear or branched divalent $C_2$-$C_{12}$ hydrocarbon-based radical, optionally including one or more heteroatoms such as oxygen; preferably, R denotes an ethylene radical, a linear or branched propylene radical, a linear or branched butylene radical or a $CH_2CH_2CH_2OCH_2CH(OH)CH_2$— radical; preferentially, R denotes a $CH_2CH_2CH_2OCH_2CH(OH)CH_2$— radical;

R', which may be identical or different, represent a linear or branched divalent $C_2$-$C_{12}$ hydrocarbon-based radical, optionally including one or more heteroatoms such as oxygen; preferably, R' denotes an ethylene radical, a linear or branched propylene radical, a linear or branched butylene radical or a radical $CH_2CH_2CH_2OCH_2CH(OH)CH_2$—; preferentially, R' denotes —$CH(CH_3)$—$CH_2$—.

The siloxane blocks preferably represent between 50 mol % and 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular mass (Mw) of the silicone is preferably between 5000 and 1 000 000 and more particularly between 10 000 and 200 000.

Mention may notably be made of the silicones sold under the name Silsoft A-843 or Silsoft A+ by Momentive.

g) and mixtures thereof.

Preferably, the amino silicones of formula (B) are chosen from the amino silicones corresponding to formula (E).

Preferably, the composition according to the invention comprises at least one amino silicone having the INCI name amodimethicone, preferably introduced in the form of an emulsion or microemulsion with surfactants.

Preferably, the composition according to the invention comprises at least one amino silicone having the INCI name amodimethicone as an emulsion or microemulsion with surfactants, having the INCI names trideceth-5 and trideceth-10.

The silicone(s) may be present in a total amount ranging from 0.01% to 20% by weight, preferably from 0.05% to 15% by weight, more preferentially from 0.1% to 10% by weight and even more preferentially from 0.5% to 5% by weight relative to the total weight of composition A and/or composition B.

The silicone(s) may be present in a total amount ranging from 0.01% to 20% by weight, preferably from 0.05% to 15% by weight, more preferentially from 0.1% to 10% by weight and even more preferentially from 0.5% to 5% by weight relative to the total weight of composition C.

The amino silicone(s) may be present in a total amount ranging from 0.01% to 20%, preferably from 0.05% to 15%, more preferentially from 0.1% to 10% and even more preferentially from 0.5% to 5% by weight relative to the total weight of composition C.

Organic Solvents

One and/or the other of the compositions A and B used in the context of the process according to the invention may comprise one or more organic solvents, different from the compound(s) containing at least one hydroxyl function as described above.

Composition A and/or composition B according to the invention is preferably aqueous. The water content may range from 20% to 99% by weight, preferably from 50% to 98% by weight and more preferentially from 60% to 95% by weight relative to the total weight of composition A and/or composition B.

Additives

One and/or the other of the compositions A and B used in the context of the process according to the invention may contain any adjuvant or additive usually used.

Among the additives that may be used, mention may be made of reducing agents, softeners, antifoams, moisturizers, UV-screening agents, peptizers, solubilizers, fragrances, anionic, cationic, nonionic or amphoteric surfactants, proteins, vitamins, polymers other than the polymers described previously, oils, waxes and mixtures thereof.

One and/or the other of the compositions A and B may notably be in the form of a suspension, a dispersion, a gel, an emulsion, notably an oil-in-water (O/W) or water-in-oil (W/O) emulsion, or a multiple emulsion (W/O/W or polyol/O/W or O/W/O), in the form of a cream, a mousse, a stick, a dispersion of vesicles, notably of ionic or nonionic lipids, or a two-phase or multi-phase lotion.

A person skilled in the art may select the appropriate presentation form, and also the method for preparing it, on the basis of his general knowledge, taking into account firstly the nature of the constituents used, notably their solubility in the support, and secondly the intended application of the composition.

Optional Application of a Composition D

The process for colouring hair keratin fibers according to the invention may also comprise a step of applying to the hair keratin fibers a composition D comprising at least one silicone compound comprising at least one carboxylic group.

Silicone Compound Bearing a Carboxylic Function

The term "carboxylic group" means a COOH or $COO^-$ functional group, the counterion of the $COO^-$ group possibly being chosen from alkali metals, alkaline-earth metals and quaternary ammoniums.

The silicones that may be used may be soluble or insoluble in composition D; they may be in the form of oil, wax, resin or gum; silicone oils and gums are preferred.

Silicones are notably described in detail in Walter Noll's *Chemistry and Technology of Silicones* (1968), Academic Press.

Preferably, the silicone compound(s) comprising at least one carboxylic group are chosen from the organosiloxanes of formula (XXVII) below:

(XXVII)

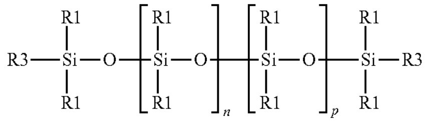

in which:

- R1 independently represents an alkyl group containing from 1 to 20 carbon atoms, preferably from 1 to 10 carbon atoms; a hydroxyl group; an alkoxy group containing from 1 to 20 carbon atoms or an aryl group containing from 6 to 12 carbon atoms;
- R2 independently represents a group R4-COOM with R4 representing a linear or branched alkylene group containing from 1 to 20 carbon atoms, preferably from 4 to 16 carbon atoms, optionally interrupted with at least one heteroatom chosen from a sulfur atom, a nitrogen atom, an oxygen atom and mixtures thereof, and M representing a hydrogen atom; an alkali metal or alkaline-earth metal or a quaternary ammonium NR'3, with R', which may be identical or different, representing H or alkyl containing from 1 to 4 carbon atoms; a pyrrolidine radical comprising a carboxylic group COOH or a group Ra-(ORb)x-COOM with Ra representing a linear or branched alkylene group containing from 1 to 4 carbon atoms, Rb representing an alkyl group containing from 1 to 4 carbon atoms, x being an integer ranging from 1 to 200; and M representing a hydrogen atom, an alkali metal or alkaline-earth metal or a quaternary ammonium $NR'_3$, with R', which may be identical or different, representing H or an alkyl containing from 1 to 4 carbon atoms;
- R3 independently represent an alkyl group containing from 1 to 20 carbon atoms; a hydroxyl group; a group R4-COOM with R4 representing a linear or branched alkylene group containing from 1 to 20 carbon atoms, preferably from 4 to 16 carbon atoms, optionally interrupted with at least one heteroatom chosen from a sulfur atom, a nitrogen atom, an oxygen atom and mixtures thereof, and M representing a hydrogen atom; an alkali metal or alkaline-earth metal or a quaternary ammonium NR'3, with R', which may be identical or different, representing H or alkyl containing from 1 to 4 carbon atoms; an alkoxy group containing from 1 to 20 carbon atoms; an aryl group containing from 6 to 12 carbon atoms or a group $R_a$—$(OR_b)_x$-COOM with $R_a$ representing a linear or branched alkylene group containing from 1 to 4 carbon atoms, $R_b$ representing an alkyl group containing from 1 to 4 carbon atoms, x being an integer ranging from 1 to 200; and M representing a hydrogen atom, an alkali metal or alkaline-earth metal or a quaternary ammonium $NR'_3$, with R', which may be identical or different, representing H or an alkyl containing from 1 to 4 carbon atoms;

n denotes an integer ranging from 1 to 1000;

p denotes an integer ranging from 0 to 1000;

it being understood that at least one of the radicals R2 and/or R3 comprises a carboxylic group COOH or COOM with M representing an alkali metal or alkaline-earth metal or a quaternary ammonium $NR'_3$, with R', which may be identical or different, representing H or an alkyl containing from 1 to 4 carbon atoms.

Notably, the silicone compound(s) comprising at least one carboxylic group may be chosen from the organosiloxanes of formula (XXVIII) below:

(XXVIII)

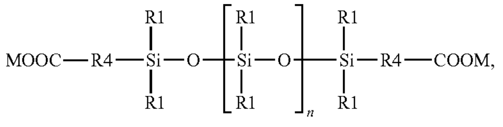

in which:

R1 independently represents a linear or branched alkyl group containing from 1 to 20 carbon atoms, preferably from 1 to 10 carbon atoms and better still from 1 to 6 carbon atoms, preferentially methyl;

R4 independently represents a linear or branched alkylene group containing from 1 to 20 carbon atoms, preferably from 4 to 16 carbon atoms, optionally interrupted with at least one heteroatom chosen from a sulfur atom, a nitrogen atom, an oxygen atom and mixtures thereof; or a divalent group $R_a$—$(OR_b)_x$— with $R_a$ representing a linear or branched alkylene group containing from 1 to 4 carbon atoms, $R_b$ representing an alkylene group containing from 1 to 4 carbon atoms, and x being an integer ranging from 1 to 200;

M independently represents a hydrogen atom, an alkali metal or alkaline-earth metal or a quaternary ammonium $NR'_3$, with R', which may be identical or different, representing H or an alkyl containing from 1 to 4 carbon atoms;

n denotes an integer ranging from 1 to 1000;

the organosiloxanes of formula (XXIX) below:

(XXIX)

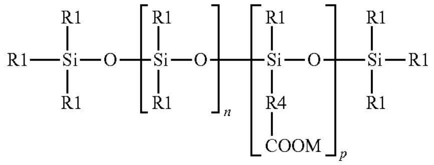

in which:

R1 independently represents an alkyl group containing from 1 to 10 carbon atoms, preferably from 1 to 6 carbon atoms, more preferentially a methyl;

R4 represents a linear or branched, saturated or unsaturated alkylene group containing from 1 to 20 carbon atoms, preferably from 4 to 16 carbon atoms, optionally interrupted with at least one heteroatom chosen from a sulfur atom, a nitrogen atom, an oxygen atom and mixtures thereof; or a divalent group $R_a$—$(OR_b)_x$— with $R_a$ representing a linear or branched alkylene group containing from 1 to 4 carbon atoms, $R_b$ representing an alkylene group containing from 1 to 4 carbon atoms, and x being an integer ranging from 1 to 200;

M represents a hydrogen atom, an alkali metal or alkaline-earth metal or a quaternary ammonium $NR'_3$, with R', which may be identical or different, representing H or an alkyl containing from 1 to 4 carbon atoms;

p denotes an integer ranging from 1 to 1000;

n denotes an integer ranging from 1 to 1000;

the organosiloxanes of formula (XXX) below:

(XXX)

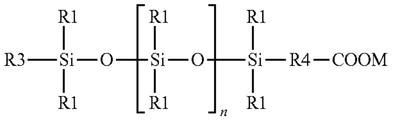

in which:

R1 independently represents an alkyl group containing from 1 to 20 carbon atoms, preferably from 1 to 10 carbon atoms and better still from 1 to 6 carbon atoms, preferentially methyl;

R4 represents a linear or branched alkylene group containing from 1 to 20 carbon atoms, preferably from 4 to 16 carbon atoms, optionally interrupted with at least one heteroatom chosen from a sulfur atom, a nitrogen atom, an oxygen atom and mixtures thereof; or a divalent group $R_a$—$(OR_b)_x$— with $R_a$ representing a linear or branched alkylene group containing from 1 to 4 carbon atoms, $R_b$ representing an alkylene group containing from 1 to 4 carbon atoms, and x being an integer ranging from 1 to 200;

R3 represents an alkyl group containing from 1 to 20 carbon atoms, an alkoxy group containing from 1 to 20 carbon atoms or an aryl group containing from 6 to 12 carbon atoms;

M independently represents a hydrogen atom, an alkali metal or alkaline-earth metal or a quaternary ammonium $NR'_3$, with R', which may be identical or different, representing H or an alkyl containing from 1 to 4 carbon atoms;

n denotes an integer ranging from 1 to 1000;

the organosiloxanes of formula (XXXI) below:

(XXXI)

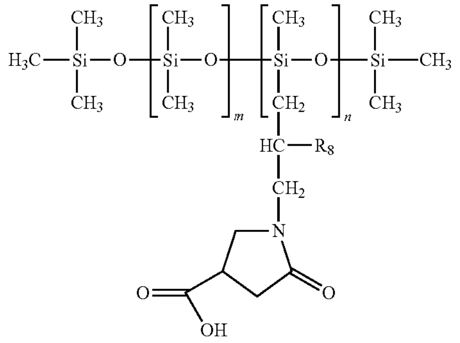

in which:

R8 represents an alkyl group containing from 1 to 6 carbon atoms, preferably a methyl;

m denotes an integer ranging from 1 to 1000;

n denotes an integer ranging from 1 to 1000;

and mixtures thereof.

Among the organosiloxanes of formula (XXVIII), mention may be made of polydimethylsiloxanes (PDMS) bearing a carboxyl end function, such as the compounds sold by the company Momentive under the trade name Silform INX (INCI name: Bis-Carboxydecyl Dimethicone).

Among the organosiloxanes of formula (XXIX), mention may be made of polydimethylsiloxanes (PDMS) bearing a carboxyl side function, such as the compounds sold by the company Shin-Etsu under the trade name X-22-3701E.

Among the organosiloxanes of formula (XXX), mention may be made of polydimethylsiloxanes (PDMS) bearing a carboxyl end function, such as the compounds sold by the company Shin-Etsu under the trade name X-22-3710.

Among the organosiloxanes of formula (XXXI), mention may be made of the compounds sold by the company Grant Industries under the trade name Grandsil SiW-PCA-10 (INCI name: Dimethicone (and) PCA Dimethicone (and) Butylene Glycol (and) Decyl Glucoside).

The silicone compounds comprising a carboxylic group may correspond, for example, to the compounds described in the patent application EP 186 507 in the name of Chisso Corporation, introduced herein by reference.

Preferably, the silicone compound(s) comprising at least one carboxylic group are chosen from the organosiloxanes of formula (XXVIII), the organopolysiloxanes of formula (XXIX) and mixtures thereof.

More preferentially, the silicone compound(s) comprising at least one carboxylic group are chosen from the organopolysiloxanes of formula (XXIXa) below:

(XXIXa)

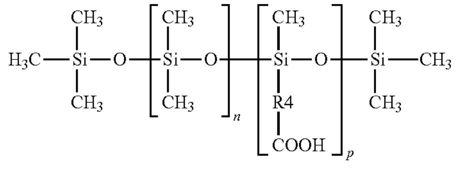

in which:

R4 represents a linear or branched, saturated or unsaturated alkylene group containing from 1 to 20 carbon atoms, preferably from 4 to 16 carbon atoms, optionally interrupted with at least one heteroatom chosen from a sulfur atom, a nitrogen atom, an oxygen atom and mixtures thereof, or even from 8 to 12 carbon atoms;

p denotes an integer ranging from 1 to 1000;

n denotes an integer ranging from 1 to 1000.

The total amount of the silicone compound(s) comprising at least one carboxylic group, present in composition D, preferably ranges from 0.01% to 20% by weight, more preferentially from 0.1% to 15% by weight and better still from 0.5% to 10% by weight relative to the total weight of composition D.

Oils

Composition D may comprise one or more oils.

Preferably, composition D comprises one or more oils. More preferentially, composition D comprises one or more oils chosen from alkanes.

The term "oil" means a fatty substance that is liquid at room temperature (25° C.) and at atmospheric pressure (760 mmHg or $1.013\times10^5$ Pa).

The oil may be volatile or non-volatile.

The term "volatile oil" refers to an oil that can evaporate on contact with the skin in less than one hour, at room temperature and atmospheric pressure. The volatile oil is a cosmetic volatile oil, which is liquid at room temperature. More specifically, a volatile oil has an evaporation rate of between 0.01 and 200 $mg/cm^2/min$, limits included (see protocol for measuring the evaporation rate indicated in the text below).

The term "non-volatile oil" refers to an oil that remains on the skin or the keratinous fibre at room temperature and atmospheric pressure. More specifically, a non-volatile oil has an evaporation rate of strictly less than 0.01 $mg/cm^2/min$ (see protocol for measuring the evaporation rate indicated in the text below).

Preferably, the composition comprises one or more oils chosen from $C_6$-$C_{16}$ alkanes and/or mixtures thereof.

As regards the $C_6$-$C_{16}$ alkanes, they may be linear or branched, and possibly cyclic.

Mention may notably be made of branched $C_5$-$C_{16}$ alkanes, such as $C_5$-$C_{16}$ isoalkanes (also known as isoparaffins), isododecane, isodecane or isohexadecane, and for example the oils sold under the Isopar or Permethyl trade names, and mixtures thereof.

Mention may also be made of linear alkanes, preferably of plant origin, comprising from 7 to 15 carbon atoms, in particular from 9 to 14 carbon atoms and more particularly from 11 to 13 carbon atoms.

As examples of linear alkanes that are suitable for use in the invention, mention may be made of n-heptane (C7), n-octane (C8), n-nonane (C9), n-decane (C10), n-undecane (C11), n-dodecane (C12), n-tridecane (C13), n-tetradecane (C14) and n-pentadecane (C15), and mixtures thereof, and in particular the mixture of n-undecane (C11) and n-tridecane (C13) described in Example 1 of patent application WO 2008/155 059 by the company Cognis.

Mention may also be made of n-dodecane (C12) and n-tetradecane (C14) sold by Sasol under the references, respectively, Parafol 12-97 and Parafol 14-97, and also mixtures thereof.

As examples of alkanes that are suitable for use in the invention, mention may be made of the alkanes described in patent applications WO 2007/068 371 and WO 2008/155 059. These alkanes are obtained from fatty alcohols, which are themselves obtained from coconut kernel oil or palm oil.

According to a particular embodiment, the composition comprises isododecane. Such a compound is, for example, the isododecane sold under the reference Isododecane by Ineos.

Preferably, composition D comprises one or more oils chosen from $C_8$-$C_{16}$ alkanes, more preferentially from isododecane, isohexadecane, tetradecane and/or mixtures thereof.

More preferentially, composition D comprises isododecane.

Composition D may comprise one or more oils present in a total amount of between 30% and 99% by weight, preferably between 50% and 99% by weight and better still between 70% and 99% by weight, relative to the total weight of composition D.

Composition D may comprise at least one colouring agent chosen from pigments, direct dyes and mixtures thereof as described previously.

Protocol

As indicated previously, compositions A and B may be applied to hair keratin fibers, such as the hair, sequentially, in any order, or simultaneously.

According to one variant of the invention, compositions A and B are applied sequentially to hair keratin fibers, such as the hair, in any order, i.e. composition A may be applied to the hair keratin fibers before composition B or vice versa.

According to a particular embodiment, the invention is a process for colouring hair keratin fibers, such as the hair, comprising:

i) the application to said hair keratin fibers of composition A or composition B, in which:

composition A comprises at least one (poly)carbodiimide compound as described previously;

composition B comprises:

at least one associative polymer as described previously;

at least one compound, different from the associative polymers, containing at least one carboxylic acid group as described previously; and at least one compound, preferably at least two compounds, containing at least one hydroxyl function;

composition A and/or composition B comprising at least one colouring agent chosen from pigments, direct dyes and mixtures thereof, one and/or the other of compositions A and B also optionally comprising at least one silicone as described previously;

ii) the application to said hair keratin fibers of composition B, if composition A was applied during step i) or of composition A if composition B was applied during step i).

Preferably, the invention is a process for colouring hair keratin fibers, such as the hair, comprising:

i) the application to said hair keratin fibers of composition A or of composition B, in which:

composition A comprises at least one (poly)carbodiimide compound as described previously;

composition B comprises:

at least one associative polymer as described previously;

at least one compound, different from the associative polymers, containing at least one carboxylic acid group as described previously; and at least one compound, preferably at least two compounds, containing at least one hydroxyl function;

composition A and/or composition B comprising at least one colouring agent chosen from pigments, direct dyes and mixtures thereof, one and/or the other of compositions A and B also optionally comprising at least one silicone as described previously;

ii) optionally a leave-on time of said composition A or of said composition B on the fibers of from 1 minute to 30 minutes, preferably from 1 to 20 minutes; and then iii) optionally a step of washing, rinsing, draining or drying said fibers, preferably a drying step, and then iv) the application to said hair keratin fibers of composition B, if composition A was applied during step i) or of composition A if the composition B was applied during step i), and then v) optionally a step of washing, rinsing, draining or drying said fibers, preferably a drying step, and then vi) the application to said hair keratin fibers of a composition D comprising at least one silicone compound comprising at least one carboxylic group as described previously; and then vii) optionally a leave-on time of said composition D on the fibers of from 1 minute to 30 minutes, preferably from 1 to 20 minutes; and then viii) optionally a step of washing, rinsing, draining or drying said fibers.

According to another variant of the invention, and preferably, compositions A and B are applied simultaneously.

According to this embodiment, compositions A and B may be mixed extemporaneously at the time of use to obtain composition C, and composition C is then applied to the hair keratin fibers, such as the hair.

Composition C and the optional composition D described above may be used on wet or dry hair keratin fibers, and also on any type of fair or dark, natural or coloured, permanent-waved, bleached or relaxed fibers.

According to a preferred embodiment, composition C and composition D are applied simultaneously to the hair keratin fibers.

According to another preferred embodiment, composition D is applied to the hair keratin fibers after applying composition C to the hair keratin fibers.

According to another preferred embodiment, composition D is applied to the hair keratin fibers before applying composition C to the hair keratin fibers.

Preferably, composition D is applied to the hair keratin fibers after applying composition C to the hair keratin fibers.

According to a particular embodiment of the invention, the hair keratin fibers are washed before applying composition C and the optional composition D.

Preferably, a washing, rinsing, draining or drying step is performed after applying composition C to the hair keratin fibers and before applying composition D to the hair keratin fibers.

More preferentially, a drying step is performed after applying composition C to the hair keratin fibers and before applying composition D to the hair keratin fibers.

The application to the fibers may be performed via any standard means, in particular using a comb, a fine brush, a coarse brush, a sponge or with the fingers.

The application of composition C and the optional composition D to the hair keratin fibers is generally performed at room temperature (between 15 and 25° C.).

After applying composition C to the hair keratin fibers, it is possible to wait for between 1 minute and 6 hours, in particular between 1 minute and 2 hours, more particularly between 1 minute and 1 hour, more preferentially between 1 minute and 30 minutes, before, for example, applying composition D to the hair keratin fibers or, for example, a washing, rinsing, draining or drying step.

Preferably, there is no leave-on time after applying composition C to the hair keratin fibers and before applying composition D to the hair keratin fibers.

After applying composition C and the optional composition D, the fibers may be left to dry or may be dried, for example at a temperature of greater than or equal to 30° C.

The process according to the invention may thus comprise a step of applying heat to the hair keratin fibers using a heating tool.

The heat application step of the process of the invention may be performed using a hood, a hairdryer, a straightening iron, a curling iron, a Climazon, etc.

Preferably, the heat application step of the process of the invention is performed using a hairdryer.

When the process of the invention involves a step of applying heat to the hair keratin fibers, the step of applying heat to the hair keratin fibers takes place after applying composition C and the optional composition D to the hair keratin fibers.

During the step of applying heat to the hair keratin fibers, a mechanical action may be exerted on the locks, such as combing, brushing or running the fingers through.

When the step of applying heat to the hair keratin fibers is performed using a hood or a hairdryer, the temperature is preferably between 30° C. and 110° C., preferentially between 50° C. and 90° C.

When the step of applying heat to the hair keratin fibers is performed using a straightening iron, the temperature is preferably between 110° C. and 220° C., preferably between 140° C. and 200° C.

In a particular variant, the method of the invention involves a step (b1) of applying heat using a hood, a hairdryer or a Climazon, preferably a hairdryer, and a step (b2) of applying heat using a straightening or curling iron, preferably a straightening iron.

Step (b1) may be performed before step (b2).

During step (b1), also referred to as the drying step, the fibers may be dried, for example at a temperature above or equal to 30° C. According to a particular embodiment, this temperature is above 40° C. According to a particular embodiment, this temperature is above 45° C. and below 110° C.

Preferably, if the fibers are dried, they are dried, in addition to a supply of heat, with a flow of air. This flow of air during drying makes it possible to improve the strand separation of the coating.

During drying, a mechanical action may be exerted on the locks, such as combing, brushing or running the fingers through.

During step (b2), the passage of the straightening or curling iron, preferably the straightening iron, may be performed at a temperature ranging from 110° C. to 220° C., preferably between 140° C. and 200° C.

After the drying step, a shaping step may be performed, for example with a straightening iron; the temperature for the shaping step is between 110 and 220° C., preferably between 140 and 200° C.

Preferably, the invention is a process for colouring hair keratin fibers, such as the hair, comprising the mixing of a composition A and of a composition B to obtain a composition C, and then:

i) the application to said hair keratin fibers of composition C, in which: composition A comprises at least one (poly)carbodiimide compound as described previously;

composition B comprises:

at least one associative polymer as described previously;

at least one compound, different from the associative polymers, containing at least one carboxylic acid group as described previously; and at least one compound, preferably at least two compounds, containing at least one hydroxyl function;

composition A and/or composition B comprising at least one colouring agent chosen from pigments, direct dyes and mixtures thereof, one and/or the other of compositions A and B also optionally comprising at least one silicone as described previously.

More preferentially, the invention is a process for colouring hair keratin fibers, such as the hair, comprising the mixing of a composition A and of a composition B to obtain a composition C, and then:

i) the application to said hair keratin fibers of composition C, in which: composition A comprises at least one (poly)carbodiimide compound as described previously;

composition B comprises:

at least one associative polymer as described previously;

at least one compound, different from the associative polymers, containing at least one carboxylic acid group as described previously; and at least one compound, preferably at least two compounds, containing at least one hydroxyl function;

at least one colouring agent chosen from pigments, direct dyes and mixtures thereof, one and/or the other of compositions A and B also optionally comprising at least one silicone as described previously, and then ii) optionally a leave-on time of said composition C on the fibers of from 1 minute to 30 minutes, preferably from 1 to 20 minutes, and then iii) optionally a step of washing, rinsing, draining or drying said fibers, and then iv) the application to said hair keratin fibers of a composition D comprising at least one silicone compound comprising at least one carboxylic group as described previously; and then v) optionally a leave-on time of said composition D on the fibers of from 1 minute to 30 minutes, preferably from 1 to 20 minutes, and then vi) optionally a step of washing, rinsing, draining or drying said fibers.

Preferably, the step of applying composition C to the hair keratin fibers is repeated several times.

According to a preferred embodiment, the process for colouring hair keratin fibers is a process for colouring hair keratin fibers such as the hair, which consists in extemporaneously mixing, at the time of use, at least two compositions A and B to obtain a composition C and in applying composition C to the hair keratin fibers, with:

composition A comprising at least one (poly)carbodiimide compound as described previously; and composition B comprising at least one associative polymer as described previously, at least one compound, different from the associative polymers, containing at least one carboxylic acid group as described previously, preferably chosen from silicone compounds comprising at least one carboxylic group, polyurethanes, acrylic polymers and mixtures thereof, at least one compound, preferably at least two compounds, containing at least one hydroxyl function, and at least one colouring agent chosen from pigments, direct dyes, and mixtures thereof.

composition A and/or composition B optionally comprising at least one silicone as defined previously.

Preferably, compositions A and B are mixed preferably less than 15 minutes before application to the hair keratin fibers, more preferentially less than 10 minutes before application, better still less than 5 minutes before application.

The weight ratio between composition A and composition B preferably ranges from 0.1 to 10, preferentially from 0.2 to 5 and better still from 0.5 to 2, or even from 0.6 to 1.5. In a particular embodiment, the weight ratio between composition A and composition B is equal to 1.

According to particular embodiment, the process for colouring hair keratin fibers is a process for colouring hair keratin fibers such as the hair, which consists in extemporaneously mixing, at the time of use, at least two compositions A and B to obtain a composition C and in applying composition C to the hair keratin fibers, with:

- composition A comprising at least one (poly)carbodiimide compound as described previously; and
- composition B comprising at least one associative polymer as described previously, at least one compound, different from the associative polymers, containing at least one carboxylic acid group as described previously, preferably chosen from silicone compounds comprising at least one carboxylic group, polyurethanes, acrylic polymers and mixtures thereof, at least one compound, preferably at least two compounds, containing at least one hydroxyl function, and at least one colouring agent chosen from pigments, direct dyes, and mixtures thereof;
- composition A and/or composition B optionally comprising at least one silicone as defined previously; and
- a composition D as described previously being applied to the hair keratin fibers before and/or after the application of composition C to the hair keratin fibers.

The present invention also relates to a device for colouring hair keratin fibers, such as the hair, comprising two compartments containing:

- in a first compartment (E1), a composition A according to the invention as defined previously;
- in a second compartment (E2), a composition B according to the invention as defined previously;
- optionally, in a third compartment (E3), a composition D as described previously.

The present invention will now be described more specifically by means of examples, which do not in any way limit the scope of the invention. However, the examples make it possible to support specific characteristics, variants and preferred embodiments of the invention.

EXAMPLES

The (poly)carbodiimide(s) of the invention are accessible via synthetic methods known to those skilled in the art starting from commercial products or reagents that can be synthesized according to chemical reactions that are also known to those skilled in the art. Mention may be made, for example, of the book *Sciences of Synthesis*-Houben-Weyl Methods of Molecular Transformations, 2005, Georg Thiem Verlag Kg, Rudigerstrasse 14, D-70469 Stuttgart, or the American U.S. Pat. No. 4,284,730 or the Canadian patent application CA 2 509 861.

More particularly, the process for preparing the (poly) carbodiimides of the invention involves, in a first step, a diisocyanate reagent (1):

$$O{=}C{=}N\text{-}L_1\text{-}N{=}C{=}O \quad (1),$$

in which formula (1) $L_1$ is as defined previously, which reacts in the presence of a carboimidation catalyst (2) such as those described in U.S. Pat. No. 4,284,730, notably phosphorus-based catalysts particularly chosen from phospholene oxides and phospholene sulfoxides, diaza- and oxaza-phospholanes, preferably under an inert atmosphere (nitrogen or argon), and in particular in a polar solvent which is preferably aprotic such as THF, glyme, diglyme, 1,4-dioxane or DMF, at a temperature between room temperature and the reflux temperature of the solvent, preferably at about 140° C.; to give the carbodiimide diisocyanate compound (3):

$$O{=}C{=}N\text{-}L_1\text{-}(N{=}C{=}N\text{-}L_1)_n\text{-}N{=}C{=}O \quad (3),$$

in which formula (3) $L_1$ and n are as defined previously. Benzoyl halogen such as benzoyl chloride may be added to deactivate the catalyst.

To obtain "symmetrical" (poly)carbodiimides, during the second step of the preparation process, compound (3) reacts with 1 molar equivalent (1 eq.) of nucleophilic reagent $R_1$—$X_1$—H and then 0.5 eq. of reagent H-E-H with $R_1$, $X_1$ and E as defined previously, to give the "symmetrical" compound (4) according to the invention:

$$[R_1{-}X_1{-}C(O){-}NH\text{-}L_1\text{-}(N{=}C{=}N\text{-}L_1)_n\text{-}NH{-}C(O)]_2\text{-}E \quad (4),$$

in which formula (4) $R_1$, $X_1$, $L_1$, n and E are as defined previously. According to one variant to obtain compound (4) from (3), it is possible first to add 0.5 eq. of reagent H-E-H and then 1 eq. of reagent $R_1$—$X_1$—H.

To obtain "dissymmetrical" (poly)carbodiimides, during the second step of the preparation process, compound (3) reacts with 1 molar equivalent (1 eq.) of nucleophilic reagent $R_1$—$X_1$—H and then 1 eq. of reagent H-E-H with $R_1$, $X_1$ and E as defined previously, to give compound (5):

$$R_1{-}X_1{-}C(O){-}NH\text{-}L_1\text{-}(N{=}C{=}N\text{-}L_1)_n\text{-}NH{-}C(O)\text{-}E\text{-}H \quad (5),$$

in which formula (5) $R_1$, $X_1$, $L_1$, n and E are as defined previously.

According to one variant to obtain compound (5) from (3), it is possible first to add 1 eq. of reagent $R_1$—$X_1$—H and then 0.5 eq. of reagent H-E-H.

During a third step, compound (5) reacts with 1 eq. of compound (6)

$R_2$—$X_2$—C(O)—NH-$L_1$-(N═C═N-$L_1$)$_z$-N═C═O (6), said compound (6) is prepared beforehand from compound (3')

$$O{=}C{=}N\text{-}L_1\text{-}(N{=}C{=}N\text{-}L_1)_2\text{-}N{=}C{=}O \quad (3'),$$

in which formula (3') $L_1$ and z are as defined previously, which reacts with 1 eq. of nucleophilic reagent $R_2$—$X_2$—H with $L_1$, $R_2$, $X_2$ and z as defined previously, to give the dissymmetrical compound (7):

$$R_1{-}X_1{-}C(O){-}NH\text{-}L_1\text{-}(N{=}C{=}N\text{-}L_1)_n\text{-}NH{-}C(O)\text{-}E\text{-}C(O){-}NH\text{-}L_1\text{-}(N{=}C{=}N\text{-}L_1)_z\text{-}NH{-}C(O){-}X_2{-}R_2 \quad (7),$$

in which formula (7) $R_1$, $X_1$, $L_1$, $R_2$, $X_2$, n, z and E are as defined previously.

It is also possible to react 1 molar equivalent of compound O═C═N-$L_1$-(N═C═N-$L_1$)$_z$-N═C═O (3') with 1/w molar equivalent of H-E-H, followed by 1 eq. of nucleophilic reagent $R_2$—$X_2$—H to give compound (8):

$$H\text{-}[E\text{-}C(O){-}NH\text{-}L_1\text{-}(N{=}C{=}N\text{-}L_1)_z]_w\text{-}NH{-}C(O){-}X_2{-}R_2 \quad (8),$$

in which formula (8) $L_1$, $R_2$, $X_2$, z and E are as defined previously, and w is an integer between 1 and 3; more preferentially, w=1.

This last compound (8) can then react with 1 eq. of compound (4'):

$R_1—X_1—C(O)—NH\text{-}L_1\text{-}(N{=}C{=}N\text{-}L_1)_n\text{-}N{=}C{=}O$ (4'), (said compound (4') being able to be synthesized by reaction of 0.5 eq. of nucleophilic reagent $R_1—X_1—H$ with 1 equivalent of compound (3)), to give the (poly)carbodiimide (9) of the invention:

$$R_1—X_1—C(O)—NH\text{-}L_1\text{-}(N{=}C{=}N\text{-}L_1)_n\text{-}NH—C(O)\text{-}[E\text{-}C(O)—NH\text{-}L_1\text{-}(N{=}C{=}N\text{-}L_1)_z]_w\text{-}NH C(O)—X_2—R_2 \quad (9),$$

in which formula (9) $L_1$, $R_1$, $X_1$, $R_2$, $X_2$, n, z, w and E are as defined previously.

The (poly)carbodiimide compounds, and similarly all the reaction intermediates and reagents, may be purified via conventional methods known to those skilled in the art, such as extraction with water and water-immiscible organic solvent, precipitation, centrifugation, filtration and/or chromatography.

Example 1: Process for Synthesizing the (poly)carbodiimide Compound 50 g of 4,4'-dicyclohexylmethane diisocyanate and 0.5 g of 4,5-dihydro-3-methyl-1-phenyl-1H-phosphole 1-oxide were placed with stirring in a 500 mL three-necked round-bottomed flask equipped with a thermometer, a stirrer and a reflux tube.

The reaction medium was heated at 140° C. under nitrogen for 4 hours, the reaction being monitored by infrared spectroscopy by means of the absorption of the isocyanate functions between 2200 and 2300 $cm^{-1}$, and then cooled to 120° C.

A mixture of 5.3 g of polyethylene glycol monomethyl ether and 1.2 g of 1,4-butanediol are introduced with stirring into the reaction medium. The temperature of 120° C. is maintained until the isocyanate functions have totally disappeared, monitored by infrared spectroscopy at 2200-2300 $cm^{-1}$, and is then cooled to room temperature.

After cooling to room temperature, the reaction medium is poured dropwise with vigorous stirring into a 500 mL glass beaker containing 85 g of distilled water, to give the desired product in the form of a translucent yellow liquid.

Example 2

Compositions A1, B1 and B2 as described below were prepared: the amounts are expressed as g of starting material as obtained/100 g.

TABLE 1

| Composition | A1 |
|---|---|
| Polycarbodiimide(1) | 24 |
| Hydroxyethyl acrylate/sodium acryloyldimethyl taurate copolymer (2) | 1 |
| Amodimethicone (and) Trideceth-5 (and) Trideceth-10 (3) | 5 |
| Preserving agent(s) | qs |
| Water | qs 100 |

(1) synthesized according to the synthetic process described in example 1 (containing 40% active material in water),
(2) sold by the company SEPPIC under the name Sepinov EMT10,
(3) sold by the company Wacker under the name Belsil ADM LOG 1 (containing 15% active material).

TABLE 2

| Composition | B1 | B2 |
|---|---|---|
| Acrylates copolymer (4) | 40 | 40 |
| Acrylates/Steareth-20 methacrylate copolymer (5) | 2 | 3 |
| Red iron oxide (CI 77491) | 12 | 12 |
| Phenoxyethanol | 0.5 | 0.5 |
| 1,2-Hexanediol | 0.75 | 0.75 |
| 4-Hydroxyacetophenone | 0.38 | 0.38 |
| Ethanol | 3.75 | 3.75 |
| Pentylene glycol | 1.88 | 1.88 |
| Chlorphenesin | 0.3 | 0.3 |
| Amodimethicone (and) Trideceth-5 (and) Trideceth-10 (3) | 5 | 5 |
| Triethanolamine | 0.67 | 1 |
| Water | qs 100 | qs 100 |

(4) sold by the company Daito Kasei Kogyo under the trade name Daitosol 3000SLPN-PE1 (aqueous dispersion containing 30% active material)
(5) sold by the company Röhm & Haas under the trade name Aculyn 22 ® (methacrylic acid/ethyl acrylate/oxyalkylenated stearyl methacrylate terpolymer) (30% active material).

Thus, compositions A1, B1 and B2 are compositions used in the context of the process according to the invention. These compositions are thus considered as compositions according to the invention.

a. Evaluation of the Stability

The appearance of the compositions is observed after they have been prepared, at T0.

Composition A1 is in the form of a smooth fluid gel.

Compositions B1 and B2 are in the form of a runny, viscous, coloured gel.

The compositions are then stored for 2 months at 45° C., at atmospheric pressure. The stability of each of the compositions is then evaluated by visual observation.

The stability of compositions A1, B1 and B2 is acceptable.

b. Evaluation of the Antimicrobial Performance

Two tests are performed in the context of this evaluation: an "orientation" test and a "confirmation" test.

Measuring Method:

The efficacy of the preserving agent according to the invention is evaluated by means of the Challenge test, which makes it possible to determine the level of antimicrobial protection of a composition.

It consists of artificial contamination of the test product with various microorganisms (bacteria, yeasts and moulds) and monitoring of the number of viable germs over time.

This is why, before the start of the test, a cleanliness control must be performed. This makes it possible to check that the formulations that are to be tested in the Challenge test are not contaminated or that they meet the tolerated standards. Thus, multiple contaminations are avoided for correct progress of the Challenge test.

A product that is satisfactorily protected must enable decontamination of the microorganisms introduced, this decontamination being more or less rapid as a function of the microbial strains, the type of product, the conditioning article, etc.

The product is distributed in as many pill bottles as there are microorganisms to be tested. A calibrated microorganism suspension is introduced into each of these bottles so as to obtain a content of $10^6$ germs per gram of product (each microorganism suspension is counted to determine the exact content inoculated in the product).

The contaminated product is stored at 32.5° C.±2.5° C. for 24 hours or for 48 hours for moulds.

The efficacy of protection of the formulations is tested on a microbial spectrum that is limited but chosen from among species that are liable to contaminate the product both during manufacture and during its use.

The microbial spectrum combines the various microorganisms used to perform a Challenge test. It comprises a Gram-positive bacterium (*Enterococcus faecalis*), a yeast (*Candida albicans*) and a mould (*Aspergillus niger*) for the orientation test and four bacteria (*Escherichia coli, Pseudomonas aeruginosa, Staphylococcus aureus* and *Enterococcus faecalis*), a yeast (*Candida albicans*) and a mould (*Aspergillus niger*) for the confirmation test.

1st Part of the Test: Orientation

This is a screening test for orienting the rest of the tests and for identifying in a short space of time the formulations that are insufficiently protected.

After 7 days of contact between the product and the germ, a sample is taken for the purpose of counting the microorganisms remaining in the product.

Detection limit via this method: 250 cfu/g

The most favourable result is thus less than 250 germs/g (absence of microbial colonies on the dishes).

2nd Part of the Test: Confirmation

Excluding special cases, only the formulations retained on conclusion of the orientation test can undergo the confirmation step.

As for the orientation, the first sample collection for counting of the microorganisms remaining in the product takes place after 7 days of contact between the product and the germ.

The major difference between the confirmation step and the orientation step is that two other sample collections will be performed so as to monitor the change in antimicrobial protection over time: a sample collection at 14 days and another at 28 days.

The dilutions made to perform the counting are seeded in Petri dishes.

The germs remaining in the product are counted.

Example: $4.3 \times 10^5$ germs/g

Detection limit of this method: 200 cfu/g

The most favourable result is thus less than 200 germs/g (absence of microbial colonies on the Petri dishes).

In order to check the stability of the antimicrobial protection over time, this test is repeated on the formulation after 2 months of accelerated ageing at 45° C.

The results are collated in the table below:

TABLE 3

| Compositions | B1 | B2 |
|---|---|---|
| Orientation test (less than 250 germs/g (absence of microbial colonies on the dishes)) | OK | OK |
| Confirmation test (less than 200 germs/g (absence of microbial colonies on the dishes)) | OK | OK |

Thus, the colouring process according to the invention uses compositions which have good stability over time and good protection against microorganisms, and thus good storage over time.

Example 3

Compositions A1, B1 and B2 as described above in Example 2 were prepared.

Two mixtures are then made.

Composition A1 is mixed with composition B1 in a 50/50 ratio to obtain composition C1.

Composition A1 is mixed with composition B2 in a 50/50 ratio to obtain composition C2.

Thus, compositions C1 and C2 are compositions according to the invention.

Next, composition D as described below was prepared: the amounts are expressed as g of starting material as obtained/100 g.

TABLE 4

| Compositions | D |
|---|---|
| Bis-carboxydecyl dimethicone (6) | 2 |
| Isododecane | qs 100 |

(6) sold by the company Momentive Performance Materials under the trade name Silform INX Protocol:

Each of the compositions C1 and C2 is applied to locks of dry natural hair containing 90% white hairs, in a proportion of 0.8 g of composition per gram of lock.

The locks of hair are then dried with a hairdryer, and then combed.

Next, composition D is applied to said locks of dry hair treated with compositions C1 and C2, in a proportion of 0.5 g of composition per gram of lock.

The locks of hair are then dried with a hairdryer, and then combed. The locks of hair are then stored at room temperature and ambient humidity for 24 hours.

The locks of hair thus coloured are then subjected to a test of several repeated shampoo washes so as to evaluate the fastness (persistence) of the colouring obtained with respect to shampoo washes, according to the shampoo washing protocol described below.

Shampoo Washing Protocol:

The coloured locks of hair are combed, moistened with water at 35° C. and then passed between the fingers five times for 5 seconds. The locks of hair are then squeezed dry between two fingers.

A standard shampoo (Garnier Ultra Doux) is applied uniformly to the coloured locks, in a proportion of 0.4 g of standard shampoo per gram of locks, the locks of hair being massaged gently along the length (6 passes) for 15 seconds, from the root to the end.

The locks of hair are then placed on a watch glass and left to stand for 1 minute.

Next, the locks of hair are rinsed with water while passing the lock between the fingers (15 passes). The locks of hair are then squeezed dry between two fingers before the next shampoo wash.

Once the tests of several shampoo washes have been performed, the locks of hair are combed and dried with a hairdryer.

Results:

The persistence of the colour of the locks was evaluated in the CIE L*a*b* system, using a Minolta Spectrophotometer CM3600A colorimeter (illuminant D65, angle 10°, specular component included).

In this L*a*b* system, L* represents the intensity of the colour, a* indicates the green/red colour axis and b* the blue/yellow colour axis.

The persistence of the colouring is evaluated by the colour difference ΔE between the coloured locks before shampooing, then after having undergone five shampoo washes according to the protocol described above. The lower the ΔE value, the more persistent the colour with respect to shampoo washing.

The ΔE value is calculated according to the following equation:

$$\Delta E=\sqrt{(L^*-L_0^*)^2+(a^*-a_0^*)^2+(b^*-b_0^*)^2}$$

In this equation, L*a*b* represent the values measured after colouring the hair and after performing the shampoo washes, and $L_0$*$a_0$*$b_0$* represent the values measured after colouring the hair but before shampoo washing.

TABLE 5

| Compositions | Number of shampoo washes | L* | a* | b* | ΔE |
|---|---|---|---|---|---|
| C1 + D (invention) | 0 | 33.4 | 28.6 | 22.3 | — |
| | 5 | 37.1 | 25.7 | 19.7 | 5.4 |
| C2 + D (invention) | 0 | 34.0 | 27.5 | 21.3 | |
| | 5 | 39.7 | 21.4 | 16.3 | 9.7 |

The locks of hair treated with each of the compositions (C1 and C2)+D and washed with five shampoo washes have low ΔE values. Thus, the coloured coating of the hair keratin fibers obtained with compositions (C1 and C2)+D shows good persistence with respect to shampoo washing.

Furthermore, smooth, uniform, coloured coating on the hair is observed.

Example 4

Compositions A2, B3 and B4 as described below were prepared: the amounts are expressed as g of starting material as obtained/100 g.

TABLE 6

| Composition | A2 |
|---|---|
| Polycarbodiimide(1) | 24 |
| Hydroxyethyl acrylate/sodium acryloyldimethyl taurate copolymer (2) | 1 |
| Preserving agent(s) | qs |
| Water | qs 100 |

TABLE 7

| Compositions | B3 | B4 |
|---|---|---|
| Acrylates copolymer (4) | 40 | 40 |
| Acrylates/Steareth-20 methacrylate copolymer (5) | 2 | — |
| Carbomer (6) | — | 1 |
| Red iron oxide (CI 77491) | 12 | 12 |
| 2-phenoxyethanol | 0.1 | 0.1 |
| Octane-1,2-diol | 0.3 | 0.3 |
| Preserving agent(s) | qs | qs |
| Water | qs 100 | qs 100 |

(6) sold by the company Lubrizol under the name Carbopol 980.

Thus, compositions A2 and B3 are compositions used in the context of the process according to the invention. These compositions are thus considered as compositions according to the invention. Composition B4 is a comparative composition.

The appearance of the compositions is observed after they have been prepared, at T0.

Composition A2 is in the form of a smooth, fluid gel.

Composition B3 is in the form of a runny, viscous gel.

Composition B4 is in the form of a very thick gel.

The compositions are then stored for 10 days at 55° C., at atmospheric pressure. The stability of each of the compositions is then evaluated by visual observation.

It is seen that composition B4 was in the form of a very brittle, dry gel with many grains.

Thus, the stability of composition B4 is unsatisfactory and unacceptable.

On the other hand, the stability of composition B3 is acceptable. The stability of composition A2 is also acceptable.

Example 5

Compositions A2 and B3 as described above in Example 4 were prepared.

Composition A2 is mixed with composition B3 in a 50/50 mass ratio to obtain a hair colour composition C3.

Thus, composition C3 is a composition according to the invention.

Next, composition D as described above in example 3 is used.

Protocol:

Composition C3 is applied to locks of dry natural hair containing 90% white hairs, in a proportion of 0.5 g of composition per gram of lock.

The locks of hair are then dried with a hairdryer, and then combed.

Next, composition D is applied to said locks of dry hair treated with composition C3, in a proportion of 0.5 g of composition per gram of lock.

The locks of hair are then left at room temperature for 24 hours.

The locks of hair thus coloured are then subjected to a test of several repeated shampoo washes so as to evaluate the fastness (persistence) of the colouring obtained with respect to shampoo washes, according to the shampoo washing protocol described below.

Shampoo Washing Protocol:

The coloured locks of hair are combed, moistened with water at 35° C. and then passed between the fingers five times for 5 seconds. The locks of hair are then squeezed dry between two fingers.

A standard shampoo (Garnier Ultra Doux) is applied uniformly to the coloured locks, in a proportion of 0.4 g of standard shampoo per gram of locks, the locks of hair being massaged gently along the length (6 passes) for 15 seconds, from the root to the end.

The locks of hair are then placed on a watch glass and left to stand for 1 minute.

Next, the locks of hair are rinsed with water while passing the lock between the fingers (15 passes). The locks of hair are then squeezed dry between two fingers before the next shampoo wash.

Once the tests of several shampoo washes have been performed, the locks of hair are combed and dried with a hairdryer.

Results:

TABLE 8

| Composition | Number of shampoo washes | L* | a* | b* | ΔE |
|---|---|---|---|---|---|
| C3 + D (invention) | 0 | 34.8 | 28.1 | 21.9 | — |
| | 5 | 42.9 | 21.4 | 16.8 | 11.7 |

The locks of hair treated with the composition C3+D and washed with five shampoo washes have low ΔE values. Thus, the coloured coating obtained with compositions C3+D shows good persistence with respect to shampoo washing.

Furthermore, smooth, uniform, coloured coating on the hair is observed.

The invention claimed is:

1. Process for colouring hair keratin fibers, comprising the application of a composition A and a composition B to said hair keratin fibers, in which:

composition A comprises at least one (poly)carbodiimide compound chosen from the compounds of formula (II) below:

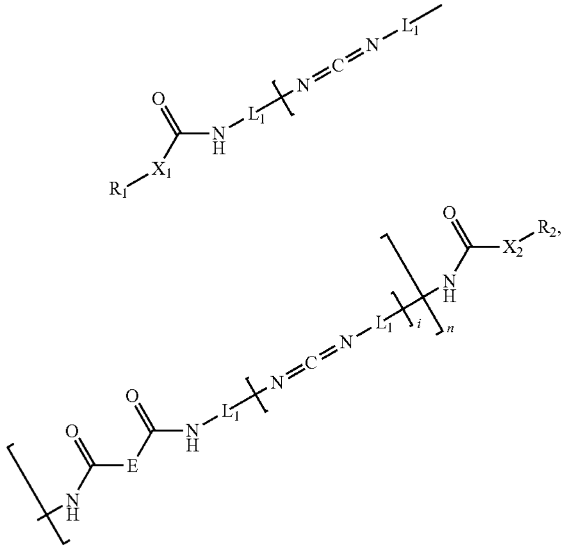

in which:

$X_1$ and $X_2$ independently represent an oxygen atom;

$R_1$ and $R_2$ are independently chosen from dialkylamino alcohols, alkyl esters of hydroxycarboxylic acid and monoalkyl ethers of (poly)alkylene glycol, in which a hydroxyl group has been removed, and mixtures thereof;

n and z denote an integer ranging from 1 to 20, with n+z≥2 and w is equal to 1;

$L_1$ is chosen from a $C_1$-$C_{18}$ divalent aliphatic hydrocarbon-based radical, a $C_3$-$C_{15}$ cycloalkylene radical, a $C_3$-$C_{12}$ heterocycloalkylene group or a $C_6$-$C_{14}$ arylene group, and mixtures thereof;

E independently represents a group chosen from: —O—$R_3$—O—; —S—$R_4$—S—; and —$R_5$—N($R_6$)—$R_4$—N($R_6$)—$R_5$—;

in which $R_3$ and $R_4$ are independently chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof;

$R_5$ independently represents a covalent bond or a saturated divalent hydrocarbon-based radical, optionally interrupted with one or more heteroatoms; and when $R_5$ is not a covalent bond, $R_5$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof; and $R_6$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof; and composition B comprises:

at least one associative polymer;

at least one compound, different from the at least one associative polymer, containing at least one carboxylic acid group; and at least one compound containing at least one hydroxyl function;

composition A and/or composition B comprising at least one colouring agent chosen from pigments, direct dyes and mixtures thereof, and in which composition A and composition B are applied simultaneously or sequentially to the hair keratin fibers.

2. Process according to claim 1, characterized in that the (poly)carbodiimide compound(s) are chosen from the compounds of formula (II) in which:

$X_1$ and $X_2$ independently represent an oxygen atom;

$R_1$ and $R_2$ are, independently, monoalkyl ethers of (poly) alkylene glycol, in which a hydroxyl group has been removed;

n and z denote an integer ranging from 1 to 20, with n+z≥2 and w is equal to 1;

$L_1$ is a $C_3$-$C_{15}$ cycloalkylene radical;

E independently represents a group chosen from: —O—$R_3$—O—; —S—$R_4$—S—; and —$R_5$—N($R_6$)—$R_4$—N($R_6$)—$R_5$—;

in which $R_3$ and $R_4$ are independently chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof;

when $R_5$ is not a covalent bond, $R_5$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof; and $R_6$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof.

3. Process according to claim 1, characterized in that the (poly)carbodiimide compound(s) are chosen from the compounds of formula (II) in which:

$X_1$ and $X_2$ independently represent an oxygen atom;

$R_1$ and $R_2$ independently represent the compound of formula (VI) below:

$$R_{13}—[O—CH_2—C(H)(R_{14})]_q— \quad (VI),$$

in which $R_{13}$ represents a $C_1$-$C_4$ alkyl group or a phenyl, $R_{14}$ represents a hydrogen atom or a $C_1$-$C_4$ alkyl group, and q denotes an integer ranging from 4 to 30;

n and z denote an integer ranging from 2 to 20, with n+z ranging from 4 to 10 and w is equal to 1;

$L_1$ is a $C_3$-$C_{15}$ cycloalkylene radical; and

E represents a group —O—$R_3$—O— in which $R_3$ is chosen from a $C_6$-$C_{14}$ arylene radical, a $C_3$-$C_{12}$ cycloalkylene radical, a linear or branched $C_1$-$C_{18}$ alkylene radical, optionally interrupted with one or more heteroatoms, and mixtures thereof.

4. Process according to claim 1, characterized in that the (poly)carbodiimide compound(s) are chosen from the compounds of formula (II) in which:

$X_1$ and $X_2$ independently represent an oxygen atom;

$R_1$ and $R_2$ independently represent the compound of formula (VI) below:

$$R_{13}—[O—CH_2—C(H)(R_{14})]_q— \quad (VI),$$

in which $R_{13}$ represents a $C_1$-$C_4$ alkyl group or a phenyl, $R_{14}$ represents a hydrogen atom or a $C_1$-$C_4$ alkyl group, and q denotes an integer ranging from 4 to 30;

n and z denote an integer ranging from 1 to 20, with n+z ranging from 4 to 10 and w is equal to 1;

$L_1$ is a $C_3$-$C_{15}$ cycloalkylene radical; and

E represents a group —O—$R_3$—O— in which $R_3$ represents a linear or branched $C_1$-$C_{18}$ alkylene radical, optionally interrupted with one or more heteroatoms.

5. Process according to claim 1, characterized in that the (poly)carbodiimide compound(s) are chosen from the compounds of formula (XII) below:

(XII)

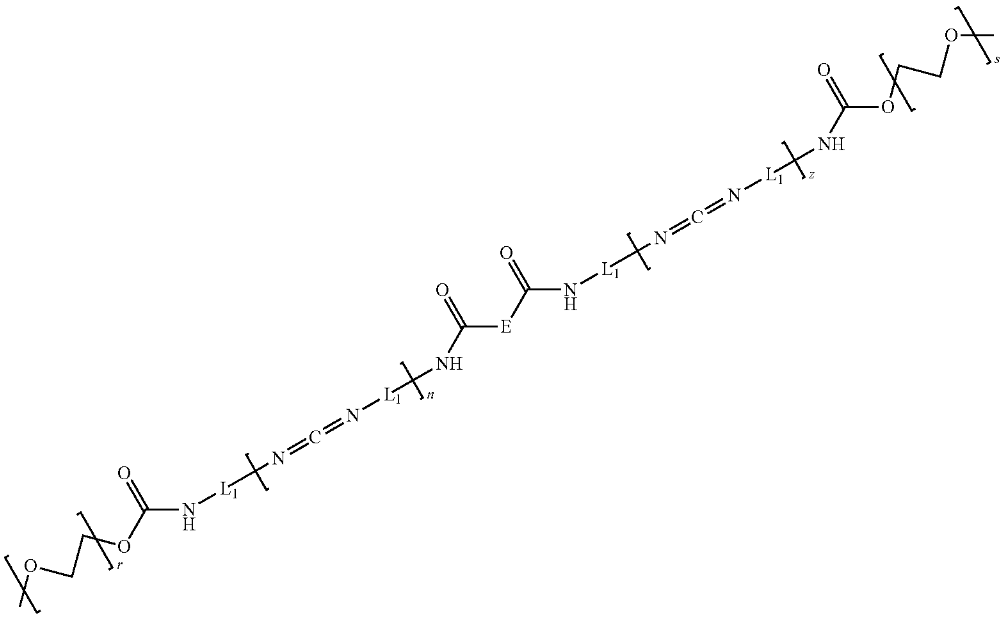

, in which $L_1$ is 4,4-dicyclohexylenemethane, n and z denote an integer ranging from 1 to 20, with n+z ranging from 4 to 10, E represents a group —O—$R_3$—O— in which $R_3$ represents a linear or branched $C_1$-$C_{18}$ alkylene radical, optionally interrupted with one or more heteroatoms, and r and s denote an integer ranging from 4 to 30.

6. Process according to claim 1, characterized in that the total amount of the (poly)carbodiimide compound(s) ranges from 0.01% to 40% by weight relative to the total weight of composition A.

7. Process according to claim 1, characterized in that the associative polymer(s) are chosen from anionic associative polymers.

8. Process according to claim 1, characterized in that the total amount of the associative polymer(s) ranges from 0.1% to 30% by weight, relative to the total weight of composition B.

9. Process according to claim 1, characterized in that the compound(s), different from the at least one associative polymer, containing at least one carboxylic acid group, are chosen from silicone compounds comprising at least one carboxylic group, polyurethanes, acrylic polymers and mixtures thereof.

10. Process according to claim 9, characterized in that the compound(s), different from the at least one associative polymer, containing at least one carboxylic acid group, are in the form of aqueous dispersions of particles of polymer(s) chosen from polyurethanes, acrylic polymers and mixtures thereof.

11. Process according to claim 10, characterized in that the acrylic polymers comprise one or more units derived from the following monomers:

a) (meth)acrylic acid; and b) $C_1$ to $C_{30}$ alkyl (meth)acrylate.

12. Process according to claim 1, characterized in that the total amount of the compound(s), different from the at least one associative polymer, containing at least one carboxylic acid group, ranges from 0.2% to 60% by weight relative to the total weight of composition B.

13. Process according to claim 1, characterized in that composition B comprises at least one compound containing at least one hydroxyl function, chosen from phenoxyethanol, 1,2-hexanediol, 4-hydroxyacetophenone, ethanol, chlorphenesin, pentylene glycol and mixtures thereof.

14. Process according claim 1, characterized in that the total content of compound(s) containing at least one hydroxyl function is at least 2% by weight relative to the total weight of composition B.

15. Process according to claim 1, characterized in that the content of colouring agent(s) ranges from 0.001% to 20% by weight relative to the total weight of composition A and/or composition B.

16. Process according to claim 1, characterized in that the content of pigments ranges from 0.05% to 20% by weight relative to the total weight of composition A and/or composition B.

17. Process according to claim 1, characterized in that composition A and/or B further comprise at least one silicone.

18. Process according claim 17, characterized in that said silicone(s) are present in a total amount ranging from 0.01% to 20% by weight relative to the total weight of composition A and/or composition B.

19. Process according to claim 1, characterized in that it also comprises a step of applying to the hair keratin fibers a composition D comprising at least one silicone compound comprising at least one carboxylic group.

20. Process according to claim 19, characterized in that the total amount of the silicone compound(s) comprising at least one carboxylic group present in composition D ranges from 0.01% to 20% by weight relative to the total weight of composition D.

21. Process according to claim 19, characterized in that composition D also comprises one or more oil(s).

22. Device for colouring hair keratin fibers, comprising at least two compartments containing compositions as defined in claim 1:

in a first compartment (E1), a composition A;

in a second compartment (E2), a composition B.

* * * * *